(12) United States Patent
Wells et al.

(10) Patent No.: US 8,679,771 B2
(45) Date of Patent: Mar. 25, 2014

(54) SPECIFIC N-TERMINAL LABELING OF PEPTIDES AND PROTEINS IN COMPLEX MIXTURES

(75) Inventors: James A. Wells, Burlingame, CA (US); Sami Mahrus, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 985 days.

(21) Appl. No.: 12/524,557

(22) PCT Filed: Jan. 24, 2008

(86) PCT No.: PCT/US2008/051951
§ 371 (c)(1),
(2), (4) Date: Feb. 17, 2010

(87) PCT Pub. No.: WO2008/092030
PCT Pub. Date: Jul. 31, 2008

(65) Prior Publication Data
US 2010/0143912 A1    Jun. 10, 2010

Related U.S. Application Data

(60) Provisional application No. 60/886,601, filed on Jan. 25, 2007.

(51) Int. Cl.
*G01N 33/535*    (2006.01)
(52) U.S. Cl.
USPC ............... 435/7.6; 435/23; 435/18; 435/68.1
(58) Field of Classification Search
None
See application file for complete search history.

(56) References Cited

U.S. PATENT DOCUMENTS

| 7,244,411 B2 | 7/2007 | Núñez et al. | |
| 2004/0115777 A1* | 6/2004 | Budworth et al. | 435/69.7 |

OTHER PUBLICATIONS

Chang et al (Subtiligase: A tool for semisynthesis of protein, 1994, PNAS, vol. 91, p. 12544-12548).*
Urbani et al (Proteomics, 2005, 5:796-804).*
Thiede et al (J of Biol Chem, 2001, 276:26055-26050).*
Chang et al (PNAS, 1994, 91:12544-12548).*
Chang et al. "Subtiligase: A tool for semisynthesis of proteins," Proc. Natl. Acad. Sci. USA, 1994, vol. 91, pp. 12544-12548.
Tolbert et al. "New Methods for Proteomic Research: Preparation of Proteins with N-Temianl Cysteines for Labeling and Conjugation." Angew. Chem. Int. Ed., 2002, vol. 41, No. 12, pp. 2171-2174.
Welker et al. "Use of Benzyl Mercaptan for Direct Preparation of Long Polypeptide Benzylthio Esters as Substrates of Subtiligase," Biochemical and Biophysical Research Communications. 1999, vol. 254, pp. 147-151.
Zappacosta et al. "N-Terminal Isotope Tagging Strategy for Quantitative Proteomics: Results-Driven Analysis of Protein Abundance Changes," Anal. Chem. 2004, vol. 76, No. 22, pp. 6618-6627.

* cited by examiner

*Primary Examiner* — Sean E Aeder
*Assistant Examiner* — Julie Wu
(74) *Attorney, Agent, or Firm* — Kilpatrick Townsend & Stockton LLP

(57) ABSTRACT

This invention provides general methods for selective labeling of proteins on their N-termini with synthetic peptides. The methods of this invention can be applied to the global proteomic profiling of complex mixtures of proteins and polypeptides.

16 Claims, 17 Drawing Sheets hGH unmodified hGH hGH
+ peptide ester
+ ligase ligated hGH

*Fig. 8d*

| dataset: | 1 | 2 | 3 | 4 | |
|---|---|---|---|---|---|
| 1 | 175 | 86 | 72 | 92 | ⎫ |
| 2 | – | 125 | 76 | 85 | ⎬ number of overlapping putative caspase substrates |
| 3 | – | – | 115 | 73 | ⎭ |
| 4 | – | – | – | 145 | |
| overlap between all = 117 | | | | | |
| summation of all = 272 | | | | | |

SPECIFIC N-TERMINAL LABELING OF PEPTIDES AND PROTEINS IN COMPLEX MIXTURES

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED AS AN ASCII TEXT FILE

The Sequence Listing written in file 81906-176610US-801036_ST25.TXT, created on Mar. 7, 2012, 4,884 bytes, machine format IBM-PC, MS-Windows operating system, is hereby incorporated by reference.

BACKGROUND OF THE INVENTION

The identification of proteins in complex mixtures is the primary goal of the field of proteomics. Proteomics seeks to understand cellular and disease processes by analyzing a plurality of proteins that number in the tens of thousands and can vary in concentration by up to 10 orders of magnitude (Qian et al., *Molecular and Cellular Proteomics* 5, 1727-1744 (2006)). The biological samples that are studied in proteomics can vary tremendously and include cultured cell lines, tissues, and bodily fluids, among others. The ability to analyze the proteomic complexity in samples such as these remains a major challenge for any study based on global biological analysis. Decreased sample complexity enables identification of a greater number of proteins in a given sample, as well as the focused identification of particular classes of proteins among a background of the full complement of proteins present in the sample. One means of achieving decreased sample complexity is through selective and site-specific labeling of discrete functional groups on proteins. Through greater proteomic coverage and identification of discrete protein subsets, such selective protein labeling methodologies enable the study of biological states as a function of time, disease, or of biological perturbation in a highly comprehensive manner.

However, chemical methods for labeling proteins suffer from a lack of specificity that results from the introduction of labels at multiple sites. For example, while one is able to label primary amine functionalities using amine reactive reagents such as succinimidyl esters, such reagents label both $\epsilon$-amines of lysines as well as $\alpha$-amines of unblocked protein N-termini. One can attempt to achieve specificity of labeling by adjusting the pH of the reaction, but this is difficult to do in practice since the pKa values for $\alpha$-amine and $\epsilon$-amines only differ by 2 pH units or less, and there are normally multiple lysines and only one N-terminus per protein. Recently, a method using pyridoxyl phosphate for selective labeling of protein $\alpha$-amines has been proposed, but this reaction is slow and does not result in labeling of N-terminal serine, threonine, cysteine, tryptophan, or proline residues (Gilmore J. M. et al., *Angew. Chem. Int. Ed.* 45, 5307-5311 (2006)).

Proper cellular function and homeostasis requires careful regulation of cellular and extracellular proteins. Protein regulation in cells and tissues is accomplished through a variety of mechanisms, including transcriptional and translational control of synthesis, as well as, through posttranslational modification of proteins. Such posttranslational protein modifications include phosphorylation, glycosylation, lipidation, ubiquitination, and proteolytic cleavage. Proteolytic processing of proteins, or proteolysis, is carried out by enzymes termed proteases that are involved in the regulation of a myriad of biological processes. These include the conversion of pre- and pro-proteins into their active forms, blood clotting, regulation of cell cycle progression, regulation of cell migration and cancer metastasis, tissue remodeling during development, programmed cell death and apoptosis, T- and B-cell development, immunity, and memory, among others. Given the complexity of these biological processes, a variety of proteases exist in cells that can process a variety of substrate proteins. Examples of regulatory proteases include caspases, matrix metalloproteases, cathepsins, calpains, granzymes, and the proteasome, among others. Each of these proteases is involved in specific biological processes that depend on the processing of specific sets of substrate proteins to result in either a gain or loss of protein substrate function, and a concomitant biological phenotype or effect.

As a specific illustration, after receiving a cell death signal, apoptotic cells execute a cellular program that results in widespread and dramatic cellular changes that can include: (1) cell shrinkage and rounding due to the breakdown of the proteinaceous cytoskeleton; (2) the appearance of a dense cytoplasm and tight packing of cell organelles; (3) chromatin condensation into compact patches against the nuclear envelope; (4) discontinuity of the nuclear envelope and DNA fragmentation; (5) breakdown of the nucleus into several discrete chromatin bodies or nucleosomal units due to the degradation of DNA; (6) blebbing of the cell membrane into irregular buds. Near the conclusion of the apoptotic program, the cell breaks apart into several vesicles called apoptotic bodies, which are then phagocytosed.

The loss of regulation of apoptosis is a hallmark of many cancer cells, which continue to divide in a malignant fashion, rather than undergoing cell death to eliminate cells that have sustained, for instance, potentially carcinogenic damage to DNA. The program of cellular degradation in apoptosis is executed in part by a family of proteases, known as the caspases. Given the profound and global cellular changes that occur during apoptosis, one would expect that a variety of substrate proteins are degraded at defined times and locations within a cell to effect this process. Knowledge of the proteins degraded in biological processes such as apoptosis, cancer cell metastasis, or memory would, thus, have a dramatic impact on the development of therapies for conditions such as cancer and memory loss, as just two examples. However, the identity and extent of the proteins degraded during proteolytic processes such as apoptosis are poorly understood. For these and other reasons, new and improved methods for identifying proteins that are substrates for proteases in a variety of biological processes in health and disease are needed. The present invention satisfies these and other needs by providing a robust method for labeling the N-termini of proteins in complex mixtures.

BRIEF SUMMARY OF THE INVENTION

The present invention provides methods for the identification of proteins in complex mixtures based on the selective labeling of protein N-termini. Thus, the present invention provides a novel mass spectrometry-based proteomic method for global profiling of proteins that is based on selective enzymatic labeling of protein N-termini using an engineered peptide ligase, permitting affinity purification and identification of corresponding N-terminal peptides.

As shown below, one application of the methods described herein is in the study of proteolysis. Proteolysis plays an important role in the regulation of diverse biological processes, but current methods for monitoring proteolytic events in complex samples are significantly more limited than those used in the study of other post-translational modifications such as phosphorylation. Moreover, the methods of the present invention can be applied to the study of apoptosis, a conserved process that is characterized by the regulated intracellular proteolysis that occurs following activation of a family of cysteine protesases termed caspases. Our combined studies have resulted in identification of 309 putative caspase cleavages sites, corresponding to 272 protein substrates, bringing the list of human proteins known to be processed by caspases from approximately 364 to 580, and validating our newly developed method as a powerful means to study proteolysis in complex samples.

Accordingly, a first embodiment of this invention provides a method for specific labeling of α-amino groups of polypeptides in complex mixtures by contacting at least one complex mixture with a labeling agent that reacts with α-amino groups of a plurality of polypeptides in the complex mixture, in which the labeling agent is subtiligase and a substrate, thus allowing the specific labeling of the α-amino groups of polypeptides in the complex mixture. In an aspect of this embodiment, a further step of detecting the plurality of polypeptides that are labeled at α-amino groups in the complex mixture is provided, thus identifying polypeptides that are present in the complex mixture.

A second embodiment of the invention provides a method of identifying proteins that undergo proteolysis by contacting a complex mixture with a first agent that blocks the N-termini of a plurality of polypeptides in the complex mixture by reacting with α-amino groups on polypeptides to generate a blocked sample, contacting the blocked sample with a second agent that provides a cellular signal to stimulate proteolysis, contacting the blocked sample with a labeling agent that reacts with α-amino groups of a plurality of polypeptides, wherein the labeling agent is subtiligase and a substrate, detecting the plurality of polypeptides that are labeled at α-amino groups in the blocked sample, thus identifying polypeptides that undergo proteolysis.

A third embodiment of the invention provides a method of identifying proteins that undergo proteolysis by contacting a first biological sample with a first agent that provides a cellular signal to stimulate proteolysis, providing a second biological sample that is a negative control, preparing an extract from the first and second samples to generate a first extract and second extract, contacting the first and second extracts with a labeling agent that reacts with α-amino groups of a plurality of polypeptides, wherein the labeling agent is subtiligase and a substrate, detecting polypeptides that are labeled at the α-amino group in the first and second extracts, and identifying polypeptides that are present in greater amounts in the first extract than in the second extract, thus identifying polypeptides that undergo proteolysis.

A fourth embodiment of the invention provides a method of identifying polypeptides in a complex mixture that are cleaved by a protease comprising the steps of contacting a complex mixture with a first agent that blocks the N-termini of a plurality of polypeptides in the complex mixture by reacting with α-amino groups on polypeptides to generate a blocked sample, adding a protease to the blocked sample, contacting the blocked sample with a labeling agent that reacts with α-amino groups of a plurality of polypeptides, wherein the labeling agent comprises subtiligase and a substrate, and detecting polypeptides that are labeled at the α-amino group in the blocked sample, thus identifying polypeptides in the complex mixture that are cleaved by a protease.

A fifth embodiment of the invention provides a method of identifying proteins that are secreted in response to a cellular signal comprising the steps of contacting a first biological sample with a first agent that provides a cellular signal to stimulate secretion, providing a second biological sample that is a negative control, collecting separately extracellular fluid surrounding the first and second biological samples, contacting extracellular fluid from the first and second biological samples with a labeling agent that reacts with α-amino groups of a plurality of polypeptides, detecting polypeptides that are labeled at the α-amino group in the extracellular fluids of the first and second biological samples, and identifying polypeptides that are present in greater amounts in the extracellular fluid of the first biological sample than in the extracellular fluid of the second sample, thus identifying polypeptides that are secreted in response to a cellular signal.

A sixth embodiment of the invention provides a method of identifying polypeptides that are differentially expressed in normal individuals and individuals with a disease, the method comprising the steps of obtaining a first biological sample from a normal individual, obtaining a second biological sample from an individual with a disease, contacting the first and second biological samples with a labeling agent that reacts with α-amino groups of a plurality of polypeptides, wherein the labeling agent is subtiligase and a substrate, detecting polypeptides that are labeled at the α-amino group in the first and second extracts, and identifying polypeptides that are present in greater or lower amounts in the sample from the individual with a disease as compared to the sample from the normal individual, thus identifying polypeptides that are differentially expressed in normal individuals and individuals with a disease.

In various aspects of the above embodiments, the substrate comprises a peptide ester with a subtiligase cleavage site. The peptide ester can further comprise a label which may be a radioisotope, a stable isotope, a fluorophore, electron dense metals, biotin, DNA, RNA, and antibody epitopes. In other aspects of the above embodiments, the substrate can further comprise a cleavable site. An example of such a cleavable site is a site for TEV protease. The protease cleavage site can comprise the amino acid sequence ENLYFQSY (SEQ ID NO:1). An example of a peptide ester that may be used in the practice of this invention is TEVEST2.

In further aspects of the above embodiments, detection can be performed using mass spectrometry, two dimensional electrophoresis, or chromatography. In other aspects, the complex mixture to be analyzed is a biological sample, which may be a cell extract. Examples of other biological samples include: cells, cell culture medium, and bodily fluids, such as serum, tissues, and animals.

In yet further aspects of the above embodiments, a cell extract is prepared from a cell treated with an agent that provides a cellular signal to stimulate proteolysis, such as an apoptotic agent. Examples of apoptotic agents can include small molecules or polypeptides. In some aspects, the apoptotic agent can be a chemotherapeutic drug such as etoposide, adriamycin, cisplatin, taxol, and bleomycin. In some aspects, two or more samples are compared, in which case, a control sample, such as an untreated cell, is provided. In some aspects, a first cell is a tumor cell and a second cell is a normal cell. Examples of such matched cells are leukemia cells and normal blood cells. Other examples of biological samples include: membrane extracts from normal and tumor cells, cell culture medium from cells treated with an agent that stimulates secretion, bodily fluids from normal and diseased individuals, and samples from different stages of embryonic development.

In an aspect of the third and fourth embodiments, the first agent is subtiligase and an acetylated peptide ester.

In an aspect of the fourth embodiment, the protease used can be serine proteases, threonine proteases, cysteine proteases, aspartic acid proteases, metalloproteases, and glutamic acid proteases. An example of a cysteine protease is a caspase.

In an aspect of the fifth embodiment, the biological sample is cells in culture and the extracellular fluid is cell culture growth media.

In an aspect of the sixth embodiment, the biological samples are bodily fluids, including serum, and the disease is cancer.

A seventh embodiment of the invention provides a method for specific labeling of α-amino groups of polypeptides in complex mixtures by contacting at least one complex mixture with a labeling agent that reacts with α-amino groups of a plurality of polypeptides in the complex mixture, where the labeling agent is subtiligase and a substrate, and the substrate comprises a peptide ester with a subtiligase cleavage site, a cleavable linker, and a label, thus specifically labeling the α-amino groups of polypeptides in a complex mixture. In an aspect of this embodiment, the method further includes the step of detecting the plurality of polypeptides that are labeled at α-amino groups in the complex mixture, thus identifying polypeptides that are present in the complex mixture. In various aspects of this embodiment, the cleavable linker can be cleaved by TEV protease and can have the amino acid sequence ENLYFQSY. In other aspects, the label can be biotin. In some aspects, the peptide ester is TEVEST2. In further aspects, the detecting step is performed using mass spectrometry.

Figure 1:
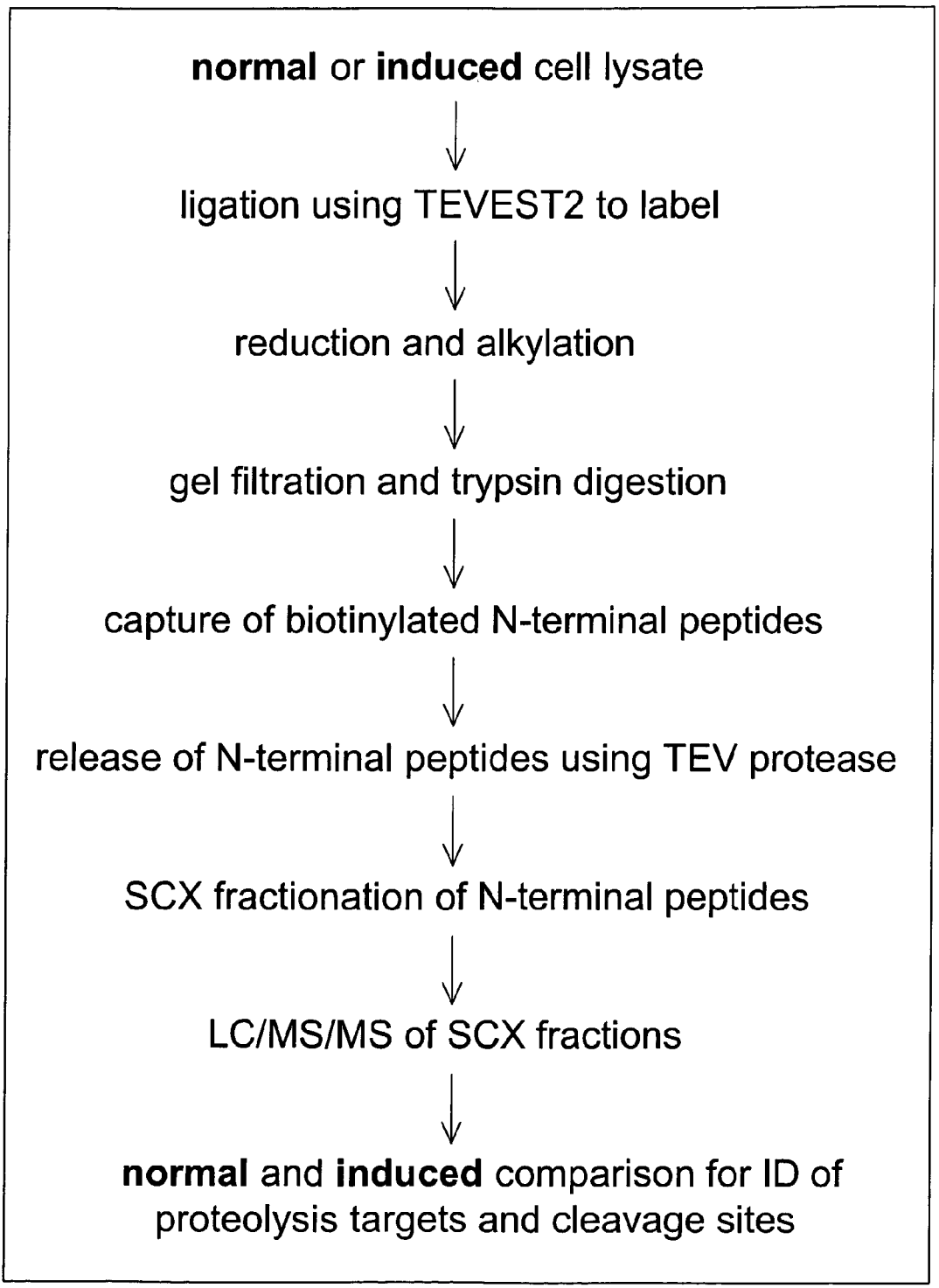
FIG. 1 shows a detailed scheme for a forward N-terminomics procedure.

GSAV, (SEQ ID NO:4), has not been previously reported. The $a_2$ and $b_2$ and ions are characteristic hallmarks of a ligated, N-terminal SY-bearing peptide. (D) Overlaps of identified putative caspase substrates between each of four different datasets are substantial, but not complete, indicating that the 272 putative caspase substrate summation from all datasets is likely only a partial sampling of available caspase substrates (datasets 1, 2, and 3 correspond to different large scale fractionation experiments, while dataset 4 corresponds to combined data from all other small scale experiments).

FIG. 9 shows Proteins containing putative caspase cleavage sites are likely true caspase substrates. (A) Functional classification of putative caspase substrates based on Gene Ontology terms indicates that they fall into classes consistent with the biology of apoptosis. (B) Sequence logo representation of the distribution of amino acids in the identified putative caspase cleavage sites. (C) Sequence logo representation of the distribution of amino acids in caspase cleavage sites reported in the literature (Luthi et al., *Cell Death Differ* 14, 641 (April, 2007)). (D) Sequence logo representation of the substrate specificity of caspase-1, representative of inflammatory caspase substrate specificity (Stennicke et al., *Biochem J* 350 Pt 2, 563 (2000); Thornberry et al., *J Biol Chem* 272, 17907 (1997)). (E) Sequence logo representation of the substrate specificity of caspase-8, representative of initiator caspase substrate specificity (Stennicke et al., *Biochem J* 350 Pt 2, 563 (2000); Thornberry et al., *J Biol Chem* 272, 17907 (1997)). (F) Sequence logo representation of the substrate specificity of caspase-3, representative of executioner caspase substrate specificity (Stennicke et al., *Biochem J* 350 Pt 2, 563 (2000); Thornberry et al., *J Biol Chem* 272, 17907 (1997)).

DETAILED DESCRIPTION OF THE INVENTION

This invention provides novel proteomic methods for the global profiling of proteins that are expressed in a variety of complex samples through the selective labeling of polypeptide N-termini. The generality of the methods of the present invention derive, in part, from the discovery of a unique method to selectively label the N-termini of proteins present in complex biological samples. By allowing the identification of the proteins thus labeled, as well as, by determining the extent of labeling, the skilled artisan is able to derive a global profile of protein expression in different biological samples. We term this general method of global profiling by labeling of polypeptide N-termini, "N-terminomics". Moreover, by comparing samples from various states such as from normal versus diseased tissues, or untreated versus drug treated states, or undifferentiated versus differentiated states, one can identify the proteins that are primarily altered between the two states. Accordingly, as discussed below, the general methods of the present invention may be applied to any of a number of settings in which a determination of differential protein expression is desired. Furthermore, the present invention can be used to determine alterations in protein expression during disease progression, stage specific protein expression during development, proteins secreted by cells in response to biological signals, the elaboration of cell surface markers in normal and diseased cells (e.g., cancer cell antigens), the serum secretion of proteins in various disease states, and proteins that undergo proteolysis under various physiological, pathological, and therapeutic states, among other applications.

In an embodiment, this invention provides novel proteomic methods for the global profiling of proteolysis in complex samples through the selective labeling of polypeptide N-termini created as a result of proteolysis. We term this global profiling method as applied to proteolysis, "degradomics". As discussed below, this method can be used to identify substrates that undergo cleavage by proteases in cells and tissues in response to a variety of signaling events. For example, the present invention can be used to generate a profile of proteins proteolyzed during the process of apoptosis which occurs in diseases such as cancer, stroke, and neurodegenerative diseases, among others. Alternatively, substrates of known proteases in complex samples can be identified by adding an exogenous protease of interest to a cell extract of a biological sample and using the methods of the present invention to identify proteins that have undergone proteolysis. The identification of substrates for proteases in various diseases where proteolysis plays a role in disease progression will provide important drug targets that may be exploited in the development of therapeutics. For example, many of the substrates cleaved in apoptosis by caspases are prosurvival factors. Such factors are important targets in cancer (e.g., topoisomerase II, Bcl-2, MEK-1, androgen receptor, BCL-ABL, EGFR, Raf-1, cyclins, XIAP, MDM-2, etc.) because cancer cells are more sensitive than normal cells to pharmacological inhibition of prosurvival factors that normally function to prevent apoptosis.

Yet another application of the methods of the present invention is in the identification of secreted proteins (e.g., growth factors) at the protein level. Yet a further application of the methods of the present invention include the identification of new biomarkers in, for instance, serum. Thus, the methods of the present invention can be used to tag and purify serum proteins that are diagnostic of different diseases or drug treated states.

Figure 2:
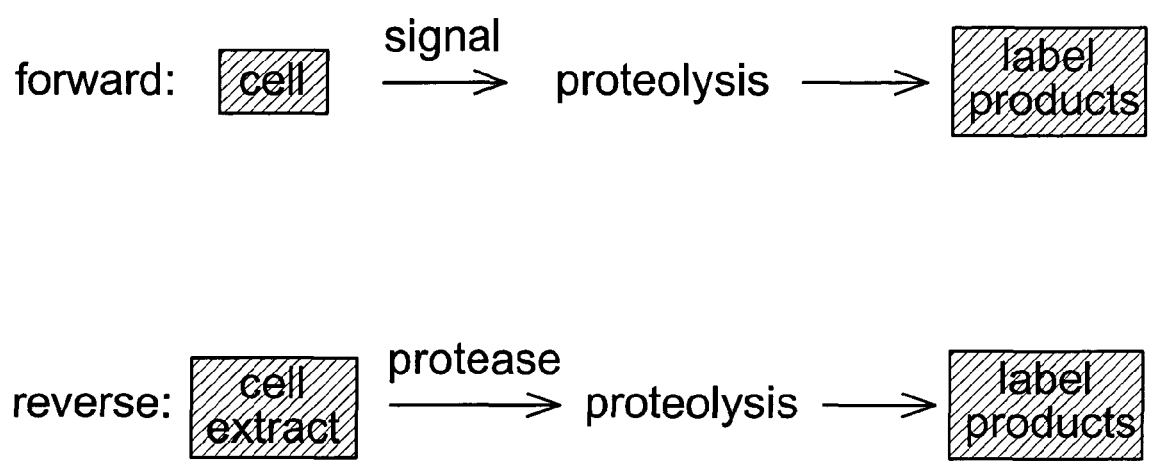
FIG. 2 shows a schematic representation of forward and reverse degradomics.
Figure 3:
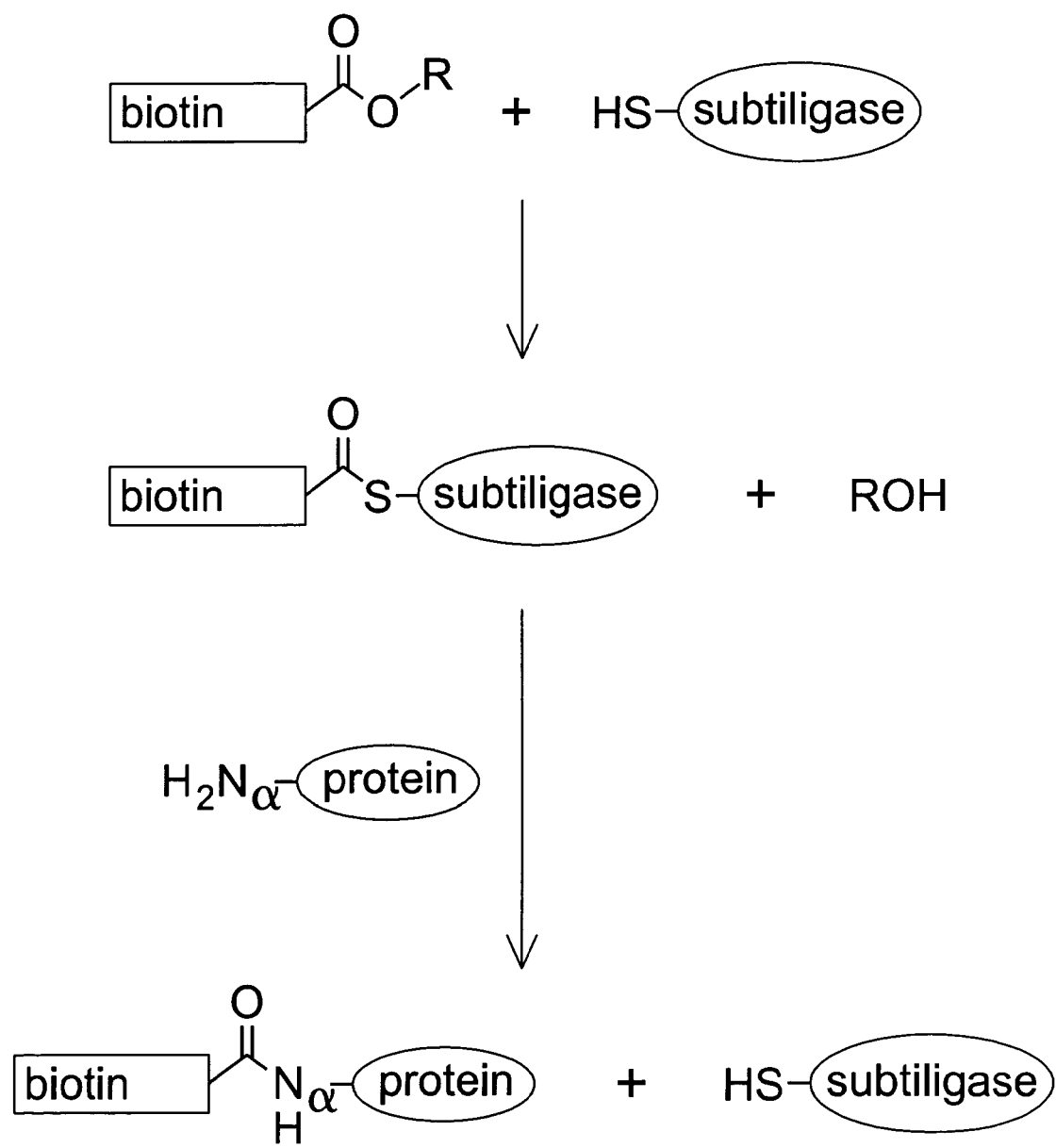
FIG. 3 shows the mechanism of subtiligase-mediated labeling of protein N-termini. The rectangle with the shaded end represents a biotinylated peptide.

More specifically, while proteins represent one of the major classes of biomolecules and serve as the basis for protein therapeutics and the field of proteomics, there are presently no reliable and effective methods to label proteins in a selective and stoichiometric fashion. Accordingly, in one embodiment of the present invention, we have developed a method that employs an enzyme called subtiligase which can selectively label proteins on their N-termini (FIG. 3). We demonstrate that this enzyme can be used for profiling proteins undergoing proteolysis in cells and cell extracts. As discussed below, the present invention can be used to study how cellular signals induce proteolysis and to globally identify protein targets that become proteolyzed ("forward degradomics") (FIG. 2). Alternatively, the methods of this invention can be used to discover proteins that become proteolyzed when one adds a specific protease to a cell extract or other biological sample ("reverse degradomics") (FIG. 2). Past proteomic technologies are inadequate to effect global profiling of proteolyzed proteins and polypeptides. Thus, in one embodiment, the current invention provides a method to label proteins that become proteolyzed using the enzyme subtiligase and an appropriately labeled substrate (e.g., a biotin labeled peptide ester). This specific labeling then permits identification and analysis of the labeled products.

In some of the Examples below, we demonstrate the utility of this invention by characterizing the proteolysis products of apoptosis. Apoptosis or programmed cell death results from post-translational pathways driven largely by widespread but controlled proteolysis. The cell biology of apoptosis is dominated by proteolytic events that are primarily mediated by caspases (i.e., Cysteine Aspartyl Protease), yet we are only beginning to understand the substrates they cleave and the complexity of the biochemical cascades they initiate. Although some caspase substrates have been identified, these have been identified piecemeal, not in a single system. Our results below suggest that the number of substrates is likely to be grossly underestimated. Currently there is no general way to globally profile the spectrum of proteins cleaved when cells undergo apoptosis (forward degradomics) or proteins that are cleaved by specific proteases when added to cell extracts (reverse degradomics). By enabling the identification of cleaved proteins and the proteases responsible, the methods of this invention allow the skilled artisan to link the overall cell biology of apoptosis with specific proteolytic events.

Figure 5A:
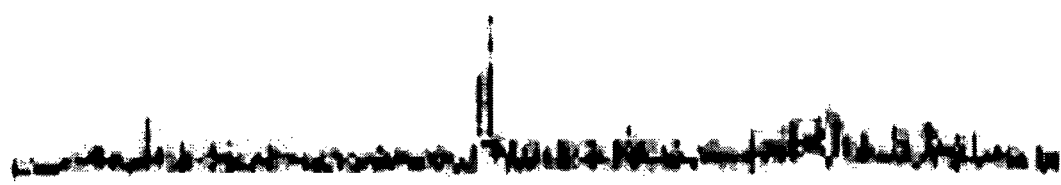
FIG. 5 shows subtiligase-mediated labeling of purified recombinant proteins in solution. (A) Recombinant human growth hormone (rhGH) was treated with subtiligase and BIOEST1, and the reaction was analyzed by ESI-TOF mass spectrometry. A single modification event per protein (+870±5 Da) indicates ligation occurs at the N-terminus and not at surface exposed lysine residues. (B) Western and avidin blotting reveals that treatment with subtiligase and BIOEST1 leads to ligation and biotinylation of recombinant PARP-1, whether in intact form (113 kDa) or after processing with recombinant caspase-7 (89 kDa).
Figure 5A:

For example, identification of specific protein substrates provides insight into the roles such proteins play in maintaining homeostasis and in driving particular cellular responses. Global profiling of proteolysis allows the skilled artisan an opportunity to determine if substrates cluster into particular signaling pathways and structural classes, and if they are involved in unexpected cellular functions. While there are a number of stimuli known to promote cell death, the role of different caspase signaling pathways in this process is not yet fully understood. Which caspases carry out which cleavage events is not known, and neither is the interplay and synergy between each of these events. Disruptions in many of the ubiquitous components of the cellular apoptotic machinery have been implicated in cancer and inflammatory diseases. A better understanding of these effects and disruptions will facilitate development of therapeutic strategies in various diseases such as cancer. A number of presently known caspase substrates are good chemotherapeutic drug targets because they are antiapoptotic, such as topoisomerases I and II, Bcl-2, MEK-1, androgen receptor, BCR-ABL, EGFR, Raf-1, cyclins, XIAP, and MDM-2. Given the importance of proteases in biology, it is important to overcome the lack of robust methods in the art for the global proteomic profiling of proteolysis. A major stumbling block for research of proteolysis in biology has been the lack of a selective labeling method that can positively enrich for cleaved proteins from the vast array of endogenous proteins in cells. Thus, in one embodiment of this invention, we have developed a novel method which uses an enzyme, subtiligase, that can ligate a biotin label onto newly exposed N-termini that result from proteolysis (FIGS. 3, 5, and 6).

A. Definitions

"Subtiligase" refers generally to proteins which have the enzymatic activity of being able to ligate esterified peptides site-specifically onto the N termini of proteins or peptides. An example of such a subtiligase is one derived from the enzyme subtilisin BPN' by site directed mutagenesis to effect the double substitution Ser221Cys and Pro225Ala, as described herein. Also described herein are additional subtiligases which have been engineered to exhibit other advantageous features, such as enhanced stability.

A "substrate" used in the context of subtiligase refers generally to any chemical moiety that is capable of being utilized during the enzymatic action of subtiligase that results in the specific labeling of the N termini of proteins or peptides by subtiligase. Examples of such substrates include peptide esters as described in greater detail herein.

"A complex mixture" refers generally to any composition that is composed of at least two or more proteins or peptides containing α-amines. A complex mixture can have at least two different proteins encoded by different genes; a complex mixture can be naturally occurring (e.g., a cell extract) or prepared (e.g., a formulation); a complex mixture can have recombinant, synthetic, or naturally occurring proteins or a mixture thereof. In many cases, a complex sample is one which displays a high degree of heterogeneity of proteins or peptides. Examples of complex mixtures include whole cells, cell extracts, partially purified cell extracts, tissues, bodily fluids, and animals, among others. Accordingly, in some embodiments, such complex mixtures comprise the naturally occurring proteins found in cells and tissues encoded by, for instance, different genes as found in the genomes of the source of the complex mixture (e.g., a cell or tissue extract or a bodily fluid such as serum). However, a complex mixture can also contain, as a component thereof, a recombinant protein or a purified protein or polypeptide either as an endogenous component (in the case of a recombinant protein), or as one added exogenously to the composition.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "cleavable linker" when used in the context of a peptide ester of the present invention refers generally to any element contained within the peptide that can serve as a spacer and is labile to cleavage upon suitable manipulation. Accordingly, a cleavable linker may comprise any of a number of chemical entities, including amino acids, nucleic acids, or small molecules, among others. A cleavable linker may be cleaved by, for instance, chemical, enzymatic, or physical means. Non-limiting examples of cleavable linkers include protease cleavage sites and nucleic acid sequences cleaved by nucleases. Further, a nucleic acid sequence may form a cleavable linker between multiple entities in double stranded form by complementary sequence hybridization, with cleavage effected by, for instance, application of a suitable temperature increase to disrupt hybridization of complementary strands. Examples of chemical cleavage sites include the incorporation photolabile, acid-labile, or base-labile functional groups into peptides.

"Proteases" (or "proteinases", "peptidases", or "proteolytic" enzymes) generally refer to a class of enzymes that cleave peptide bonds between amino acids of proteins. Because proteases use a molecule of water to effect hydrolysis of peptide bonds, these enzymes can also be classified as hydrolases. Six classes of proteases are presently known: serine proteases, threonine proteases, cysteine proteases, aspartic acid proteases, metalloproteases, and glutamic acid proteases (see, e.g., Barrett A. J. et al. The Handbook of Proteolytic Enzymes, 2nd ed. Academic Press, 2003).

Proteases are involved in a multitude of physiological reactions from simple digestion of food proteins to highly regulated cascades (e.g., the cell cycle, the blood clotting cascade, the complement system, and apoptosis pathways). It is well known to the skilled artisan that proteases can break either specific peptide bonds, depending on the amino acid sequence of a protein, or break down a polypeptide to constituent amino acids.

Among the proteases of this invention are "caspases", a family of cysteine proteases, which cleave other proteins after an aspartic acid residue. Many of the caspases are held in an inactive form as a zymogen until they are activated by proteolytic cleavage, which converts the inactive caspase into an active conformation, allowing caspase cleavage of downstream targets. Caspases serve an essential role in apoptosis, in which a cascade of sequential caspase activation is responsible executing programmed cell death. See, e.g., Thornberry, N. L. and Lazebnik, Y., *Science,* 281:1312-1316 (1998); Shi, Y., *Cell,* 117:855-8 (2004) for reviews. As an example of this regulatory hierarchy, caspase-3 is processed into an active form through its proteolysis by caspases-8, -9, and -10. Upon activation, caspase 3 is then able to activate caspases-6 and -7 via proteolysis. Caspases-3, -6, and -7 are then able to proteolyze cellular substrates such as nuclear lamins. Caspases can also become inappropriately and acutely activated during stroke, myocardial infarction, or Parkinson's disease.

"Apoptosis" refers generally to a process of programmed cell death and involves a series of ordered molecular events leading to characteristic changes in cell morphology and death, as distinguished from general cell death or necrosis that results from exposure of cells to non-specific toxic events such as metabolic poisons or ischemia. Cells undergoing apoptosis show characteristic morphological changes such as chromatin condensation and fragmentation and breakdown of the nuclear envelope. As apoptosis proceeds, the plasma membrane is seen to form blebbings, and the apoptotic cells are either phagocytosed or else break up into smaller vesicles which are then phagocytosed. Typical assays used to detect and measure apoptosis include microscopic examination of cellular morphology, TUNEL assays for DNA fragmentation, caspase activity assays, annexin-V externalization assays, and DNA laddering assays, among others. It is well known to the skilled artisan that the process of apoptosis is controlled by a diversity of cell signals which includes extracellular signals such as hormones, growth factors, cytokines, and nitric oxide, among others. These signals may positively or negatively induce apoptosis. Other effectors of apoptosis include oncogenes (e.g., c-myc) and exposure of cancer cells to chemotherapeutic agents, among other examples.

"Inducing apoptosis" or "inducer of apoptosis" refers to an agent or process which causes a cell to undergo the program of cell death described above for apoptosis.

A "cell signal" refers to any agent which may initiate or stimulate directly or indirectly proteolysis within a cell. Examples of cell signals include agents that cause cells to undergo apoptosis such as those discussed above. In the context of this invention, a cell signal may include introduction of an activated or overexpressed oncogene, such as c-myc, or any other protein that causes a proteolytic event to occur within cells, as well as, externally applied agents (e.g., chemotherapeutic drugs, etc.).

A "peptide ester" refers generally to any peptide in which one carboxyl group of the peptide is esterified, i.e., is of the structure —CO—O—R. In embodiments of this invention, a peptide ester can serve as a substrate for subtiligase such that the peptide is added to the α-amino group of polypeptides to form the structure —CO—NH—R, thus labeling the polypeptide. In some embodiments of this invention, a peptide ester can carry a detectable label and a site for proteolysis or another form of chemical cleavage (e.g., through introduction of photolabile, acid-labile, or base-labile functional groups).

A "label" or "detectable label" or "tag" is a composition detectable by mass spectrometric, spectroscopic, photochemical, biochemical, immunochemical, or chemical means. For example, useful labels include radioactive isotopes (e.g., 3H, 35S, 32P, 51Cr, or 125I), stable isotopes (e.g., 13C, 15N, or 18O), fluorescent dyes, electron-dense reagents, enzymes (e.g., alkaline phosphatase, horseradish peroxidase, or others commonly used in an ELISA), biotin, digoxigenin, or haptens or epitopes and proteins for which antisera or monoclonal antibodies are available. In general, a label as used in the context of the present invention is any entity that may be used to detect or isolate the product of the subtiligase ligation reaction. Thus, any entity that is capable of binding to another entity may be used in the practice of this invention, including without limitation, epitopes for antibodies, ligands for receptors, and nucleic acids, which may interact with a second entity through means such as complementary base pair hybridization.

"Biological sample" as used herein is a sample of cells, biological tissue, or fluid that is to be tested for the occurrence of proteolysis or the presence, more generally, of polypeptides of interest in the sample. Among the cells that can be examined are cancer cells, cells stimulated to under apoptosis, and cells at different stages of development, among others. The biological tissues of this invention include any of the tissues that comprise the organs of an organism. The biological sample can be derived from any species including bacteria, yeasts, plants, invertebrates, and vertebrate organisms. The fluid of this invention can be any fluid associated with a cell or tissue. Such fluids may include the media in which cells are cultured as well as the fluid surrounding tissues and organs, as well as the fluid comprising the circulatory system of invertebrates and vertebrates (e.g., body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like). An "extracellular fluid" refers generally to any fluid found exterior to cells. Such fluids may include all of the fluids described above.

A "negative control" has the definition recognized by the skilled artisan and generally refers to an experiment in which the desired result is no effect. Conversely, a "positive control" is a control experiment in which the desired outcome is a well-defined or well-known effect. In the context of this invention, a negative control may be a biological sample which is not treated with an agent that provides a cell signal to stimulate proteolysis or may be a sample treated with a placebo.

"Secreted protein" refers generally to any protein that is synthesized by a cell for export to the exterior of the cell membrane, for instance, secretion to the extracellular fluid. A variety of secreted proteins are recognized by the skilled artisan including: hormones, growth factors, antibiotics, antibodies, neuropeptides, toxins, cytokines, apolipoproteins, proteases and protease inhibitors, among others.

"Disease" or "disease state" refers generally to any derangement of normal physiology. Examples of diseases relevant to the practice of this invention include, without limitation: inflammatory diseases such as rheumatoid arthritis, osteoporosis, inflammatory bowel syndrome, asthma; cardiovascular diseases such as ischemia, stroke, myocardial infarction, congestive heart failure, atherosclerosis; type I and II diabetes and diabetes related diseases such as hyperglycemia, diabetic retinopathy, peripheral neuropathy; thrombotic disorders, such as diseases affecting blood clotting or complement fixation; neurodegenerative diseases such as Alzheimer's disease, Parkinson's disease, Huntington's disease, age-related dementia; liver diseases, such as liver infection, fibrosis, cirrhosis; kidney infection, fibrosis, and cirrhosis; muscular dystrophy; multiple sclerosis; lung diseases, such as lung fibrosis; schizophrenia and other mental disorders; and disorders of cell proliferation such as psoriasis and cancer (see below). (See, generally, Harrison's Principles of Internal Medicine, 16th edition, 2004.)

"Cancer" and "cancer cells" refers generally to human and animal cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers, among others.

"Chemotherapeutic drugs or agents" include conventional chemotherapeutic reagents such as alkylating agents, antimetabolites, plant alkaloids, antibiotics, and miscellaneous compounds e.g., cis-platinum, CDDP, methotrexate, vincristine, adriamycin, bleomycin, and hydroxyurea, as well as biologics, such as therapeutic antibodies. Chemotherapeutic agents can include other therapeutic approaches known in the art for treating cancer, such as radiation therapy. Chemotherapeutic drugs or agents can be used alone or in combination in the practice of the present invention.

B. Preparation of Cell Extracts

In general, any method of making an extract from cells or tissues from a biological sample that preserves the ability to label the N-termini of polypeptides with the reagents described below may be used in the practice of this invention. Any of a number of such methods are known in the art and are described in standard sources (see, e.g., Scopes, Protein Purification: Principles and Practice (1982)). In general, cells are disrupted to release and solubilize intracellular contents, followed by centrifugation to remove insoluble material, such as cell membranes and organelles. For tissue culture cells, a lysis buffer which may contain a detergent (e.g., Triton X-100, NP-40, among others) may be used. For adherent tissue culture cells, cell disruption can be accomplished by the process of scraping cells in the presence of the lysis buffer from culture plates using, for example, a rubber policeman. Other mechanical means can also be used to effect cell disruption. For example, cells can be lysed using a Dounce homogenizer. As recognized by the skilled artisan, additional mechanical means may be needed to prepare cell extracts from tissues, such as homogenization in a blender or sonication. (See, generally, e.g., Scopes, Protein Purification: Principles and Practice (1982).)

C. Labeling of N-termini of Polypeptides

The labeling of polypeptides can be accomplished using any method that labels the N-terminus (i.e., α-amino group) of a polypeptide present in a complex mixture.

In one embodiment of this invention, the labeling is accomplished using the enzyme subtiligase, which is derived from the enzyme subtilisin BPN' by converting the catalytic residue, Ser-221, to a cysteine residue, and Pro-225 to an alanine residue. The resulting double mutant protein provides the enzymatic activity of ligation of esterified peptides site-specifically onto the N termini of proteins or peptides (see, e.g., Chang, T. K. et al., *Proc. Natl. Acad. Sci. U.S.A.*, 91, 12544-12548 (1994)). Furthermore, additional forms of subtiligase that exhibit increased stability have been generated through the introduction of additional site directed mutations into the sequence (e.g., Met-50 to Phe, Asn-76 to Asp, Asn-109 to Ser, Lys-213 to Arg, and Asn-218 to Ser). Such mutant enzymes have also been termed stabiligases and may also may be used in the practice of the present invention (see, e.g., Chang, T. K. et al., *Proc. Natl. Acad. Sci. U.S.A.*, 91, 12544-12548 (1994)).

All of the earlier work describing the use of subtiligase and its variants disclosed the ligation of peptides and proteins in non-complex samples composed of single purified polypeptides. In this earlier work, two examples of the application of subtiligase to the ligation of proteins that were recombinantly expressed on the surface of phage particles were shown. For example, the work of Chang et al. demonstrated the ligation of phage-displayed human growth hormone variants that were randomized at the first three residues (Chang, T. K. et al., *Proc. Natl. Acad. Sci. U.S.A.*, 91, 12544-12548 (1994)). The work of Atwell et al. demonstrated the autoligation of phage-displayed subtiligase variants that contained an N-terminal extension and were randomized at up to five different residues outside of this N-terminal extension (Atwell S. et al., *Proc. Natl. Acad. Sci. U.S.A.*, 96, 9497-9502 (1999)). In contrast, the present invention represents a major advance, as it applies subtiligase to the ligation of polypeptides in complex mixtures of endogenous proteins as found in a variety of biological samples, not merely to simple formulations of recombinant proteins, as shown by the earlier studies. The modest amount of sample complexity in the earlier reported phage display experiments arises from minor genetic manipulations of either the human growth hormone gene or the subtiligase gene. In contrast, the complexity found in the biological samples of the present invention arises from the fact that the component polypeptides of the complex mixtures of the invention are products of a plurality of endogenous genes, which are subject to transcriptional, translational, and post-translational modulation of expression.

Furthermore, the work of Chang et al. demonstrated that subtiligase is very dependent on the primary and secondary structure of polypeptide substrates. Although subtiligase was found to exhibit broad specificity for peptide substrates, some N-terminal residues in these substrates were found to be exceedingly more preferred than others. Structural occlusion of N-termini in a protein substrate was also found to drastically affect ligation efficiency. This earlier work indicated limitations to this approach for labeling a plurality of polypeptides in complex mixtures and provided no indication of applicability to more complex samples, as the only substrates used in addition to short peptides were recombinant human growth hormone and subtiligase. In fact, those of skill in the art recognized several potential pitfalls in the implementation of subtiligase as a tool for selective labeling of polypeptide α-amines in complex mixtures. First, it was believed that only the most abundant proteins in the sample would be labeled. Second, the previous data indicated the possibility that only the most efficient substrates, based on the identity of N-terminal residues, would be labeled. Third, there existed the possibility of poor labeling of mixtures due to structural occlusion of N-termini. Fourth, there was a strong possibility that complex samples would contain inhibitors of subtiligase. Fifth, there was a prevalent concern that the peptide glycolate ester reagents would not be stable in biological samples because of the action of endogenous esterases and proteases.

However, as demonstrated below, the inventors have surprisingly found that these many pitfalls could be circumvented and have demonstrated that subtiligase may be used to efficiently label the N-termini of a plurality of polypeptides in complex mixtures, such as cell extracts and serum. For example, the inventors show that addition of a cocktail of inhibitors sufficiently blocks endogenous proteases and esterases without inhibiting subtiligase, thus, allowing for sufficient substrate to be available for ligation. Another advantage imparted by the present invention is the nature of the labeled peptide ester reagents used here. The inventors have designed versions of these reagents that are optimized for use in proteomic studies. Among other innovations, they have found that incorporation of a cleavable linker into these reagents greatly facilitates purification of labeled polypeptides from complex mixtures and subsequent analysis by tandem mass spectrometry for identification of the corresponding proteins.

Additional variants of subtiligase enzymes that have enhanced activity have also been selected through the application of phage display methods (see, e.g., Atwell, S. et al., *Proc. Natl. Acad. Sci. U.S.A.*, 96:9497-502 (1999)). Such variants may also be used in the practice of the present invention. Furthermore, other subtilisin-like enzymes and their variants may also be engineered to be used in the practice of this invention.

Subtiligase has been used to incorporate a variety of label moieties into proteins and polypeptides, including affinity handles (e.g., biotin), immunoprobes, isotopic labels, heavy-atom derivatives, PEG moieties, and other non-natural constituents (see, e.g., Chang, T. K. et al., *Proc. Natl. Acad. Sci. U.S.A.*, 91, 12544-12548 (1994)). The skilled artisan will recognize that this is not an exhaustive list, as for instance, any detectable label that can be incorporated into a substrate (e.g., biotin labeled peptide esters) to be used to label a free N-terminus (e.g., α-amino group of a polypeptide generated through proteolysis) may be used. In particular, any of the labels disclosed above may be used in the practice of the present invention.

Figure 4:
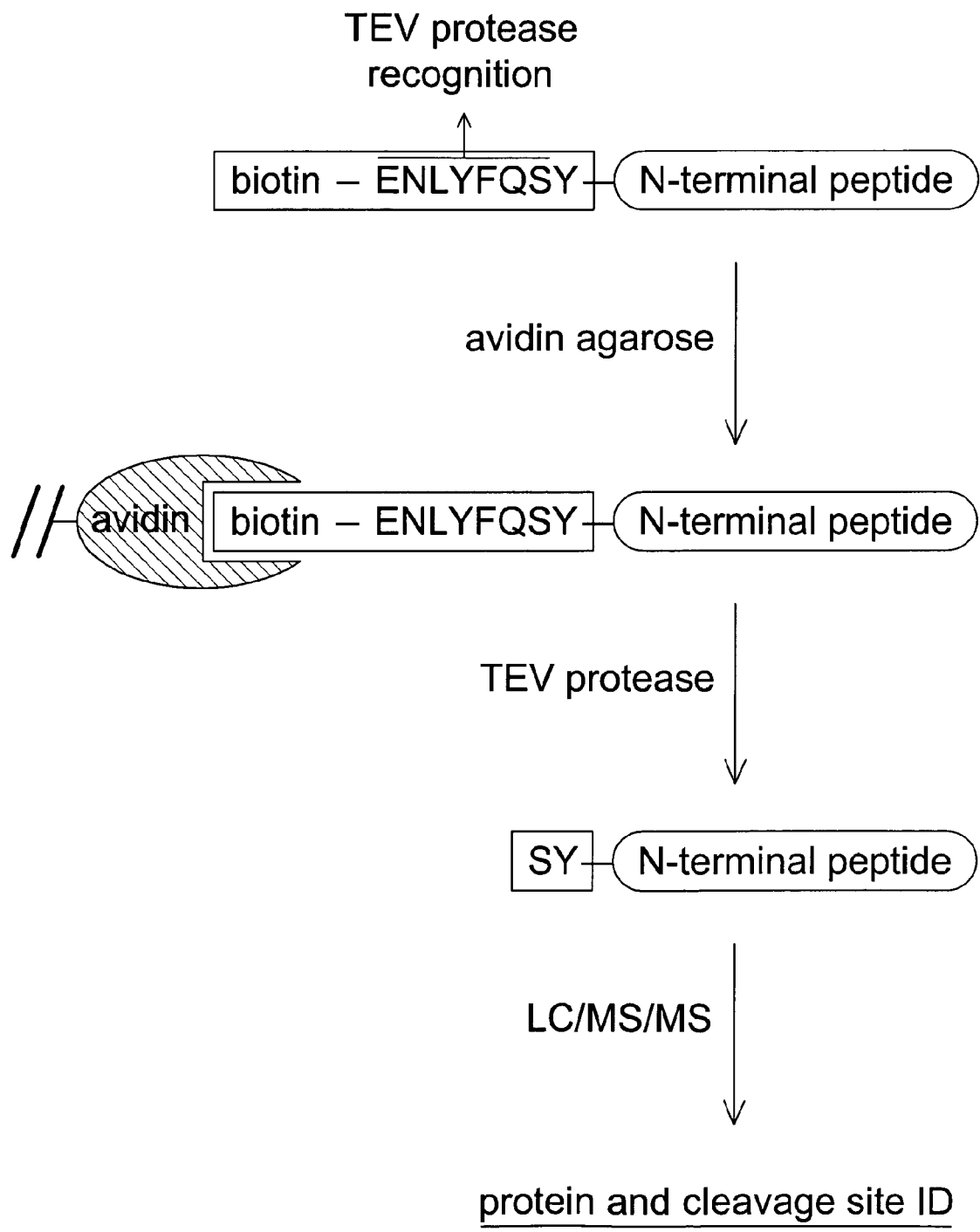
FIG. 4 shows the capture and release of subtiligase-labeled N-terminal peptides for analysis by tandem mass spectrometry. These peptides are obtained after extensive digestion of labeled proteins in cell lysates using a protease of broad specificity such as trypsin.

The reaction by which subtiligase may be used to label a free N-terminus of a polypeptide is illustrated in FIGS. 3, 4, and 6 with a biotin labeled peptide ester as the substrate for the introduction of a biotin label onto a protein. In the first step of this reaction, a free sulhydryl group on subtiligase serves as a nucleophile to effect a nucleophilic attack on the carbonyl carbon atom of the ester moiety of the substrate peptide ester, resulting in the release of an alcohol leaving group (FIG. 3). In a second step, the carbonyl carbon of the thioester linkage between the peptide substrate and the subtiligase enzyme is then subject to nucleophilic attack by the α-amino group of a protein or peptide. This reaction results in a covalent adduct comprising the biotin labeled peptide linked to the α-amino group on a protein or peptide via an amide bond (FIG. 3). Accordingly, the biotin label then can serve as an affinity handle to allow the identification and isolation of polypeptides that have a free N-terminus or free α-amino group (e.g., protein fragments that have resulted from proteolysis, or native non-acetylated or otherwise N-terminally blocked proteins).

In general, any peptide ester with the following generic elements may be used in the practice of the present invention: label-linker-peptide sequence-esterified carboxyl terminus. The skilled artisan will recognize that the location of the label within this structure may be varied without affecting the operation of the present invention. The generic structure of these elements may optionally contain a protease cleavage site or other cleavable moiety to facilitate the ready removal of the label added to the α-amino group of a protein or polypeptide. Such removal also greatly facilitates downstream mass spectrometric analysis of labeled proteins or polypeptides. FIG. 6 shows a representative peptide ester that may be used in the practice of the invention. In this example, there is a biotin label at the N-terminus of the peptide ester, a site for a protease cleavage (TEV protease), and an esterified carboxyl terminus, which serves as a subtiligase cleavage site (i.e., the site for the nucleophilic attack by a free sulfhydryl group on subtiligase as described above). Among the peptide sequences that may be used in the practice of the invention include, but are not limited to: ENLYFQSY (SEQ ID NO:1), ENLYFQSK (SEQ ID NO:5), ENLYFQSA (SEQ ID NO:6), AAPY (SEQ ID NO:7), AAPK (SEQ ID NO:8), and AAPA (SEQ ID NO:9), among others. Optional protease cleavage sites that may be used in the practice of this invention include, but are not limited to: the site for TEV protease: EXXYXQ (S/G/A), where X corresponds to any amino acid; the site for rhinovirus 3C protease: E(T/V)LFQGP (SEQ ID NO:10); the site for enterokinase: DDDDK (SEQ ID NO:11); the site for Factor Xa: I(D/E)GR; the site for thrombin: LVPR (SEQ ID NO:12); the site for furin: RXXR, where X corresponds to any amino acid; and the site for Granzyme B: IEPD (SEQ ID NO:13). Some examples of the many possible moieties that may be used to esterify the carboxyl terminus of the peptide are: HO—CH2—CO—X, where X is any amino acid, in the case of glycolate esters; HO—CHCH3—CO—X, where X is any amino acid, in the case of lactate esters; HO—R, where R is an alkyl or aryl substituent; and HS-R, where R is an alkyl or aryl substituent. A number of label moieties may be used, including radioisotopes, stable isotopes, flurophores, heavy metals, and biotin, among others.

In general, any reaction conditions that favor nucleophilic attack of a carbonyl group at an ester or thioester linkage to result in the release of the relevant leaving group (e.g., an alcohol in step one or the —SH group of subtiligase in step two) may be used in the practice of this invention for the labeling of free α-amino groups. Generally, any conditions under which ester reagents are stable to degradation and hydrolysis in complex samples; conditions under which subtiligase is stable and active; and conditions under which protein and polypeptide N-termini are free and available to react with the thioester linkage formed after the reaction of subtiligase with ester reagents are favored for the practice of this invention.

In some embodiments of this invention, the pre-existing unblocked α-amino groups of polypeptides may be blocked with a suitable N-termini blocking agent before an experimental treatment. Thus, for instance, the free, unblocked N-termini of cellular proteins may be blocked with any reagent that reacts with free α-amino groups prior to exposure of a biological sample to an agent, such as a chemotherapeutic agent, which promotes a physiological response of interest, such as apoptosis. After the experimental treatment, the newly exposed N termini which have resulted from the proteolytic events that accompany apoptosis can then be labeled using subtiligase and the ester substrates of the present invention. Examples of such blocking agents include: amine-reactive reagents such as succinimidyl esters, isothiocyanates, sulfonyl chlorides, and aldehydes, among others, provided these reagents do not contain primary or secondary amine moieties. In one embodiment, the blocking reaction can be accomplished using subtiligase and an acetylated ester.

It will be appreciated that the methods of the present invention can be used to compare the profile of labeling between two or more samples. In such contexts, for example, one sample may serve as a negative control, by being untreated, while a second sample may be treated with an agent that provides a cellular signal to stimulate proteolysis. Alternatively, the two or more samples may represent different time points of treatment, different cell types (e.g., normal versus tumor cells), or different stages of a process such as embryonic development.

It will be appreciated by the skilled artisan that a variety of complex samples can be labeled using the methods and compositions of the present invention. Such samples may include, without limitation, whole cells, cell extracts, media from cell cultures, serum from humans or animals, and other bodily fluids, among others. For example, the culture medium of cells stimulated with an agent that causes polypeptide secretion can be labeled using the methods of the present invention to identify polypeptides that have been secreted. As another example, proteins found on the surfaces of intact cells may be labeled to identify cell surface proteins, such as membrane proteins. The comparison of the cell surface proteins labeled in normal versus transformed cells can be used to identify, for example, tumor specific antigens. As a further example, serum or other bodily fluids from normal subjects and patients suffering from various diseases can be labeled to identify proteins that are unique to the serum of a patient population. The proteins so identified can serve as easily detected disease markers to be used in disease diagnostics.

D. Detection of Labeled Polypeptides

After the labeling reaction, any method that allows the detection of labeled polypeptides may be used to identify, isolate, or analyze the labeled polypeptides. For example, the skilled artisan will recognize that α-amino groups of polypeptides labeled with a peptide ester containing a biotin label can be isolated or detected using avidin-related proteins such as avidin itself, streptavidin, and neutravidin. Thus, neutravidin beads may be used to isolate biotin labeled polypeptides from complex mixtures or streptavidin linked to horseradish peroxidase may be used to identify biotin labeled polypeptides after protein separation by a procedure such as electrophoresis and avidin blotting (see, e.g., FIG. 5).

Alternatively, methods such as mass spectrometry may be used to identify peptides that are labeled following proteolysis. As understood generally by those skilled in the art, mass spectrometry is an analytical technique used to measure the mass-to-charge ratio of gaseous ions. It can be used to determine the composition of a biological sample by generating a mass spectrum representing the masses of sample components such as peptides and proteins. It can additionally be used to determine the structure of components in mixtures by observing the fragmentation of each peptide or protein present in the sample. (See, generally, *Methods in Enzymology*, Volume 402, pages 1-478, edited by A. L. Burlingame.)

For the analysis of proteins and peptides, the two primary methods for ionization of samples are used: electrospray ionization (ESI) and matrix-assisted laser desorption/ionization (MALDI). In one method of analysis, intact proteins are ionized by either of the two techniques described above, and then introduced directly to a mass analyser. In a second method, proteins are enzymatically digested into smaller peptides using an agent such as trypsin or pepsin. The collection of peptide products is then introduced to the mass analyser. This latter method is often referred to as the "bottom-up" approach of proteomic analysis.

The labeled proteins and polypeptides of the present invention can be part of a very complex mixture of other proteins, polypeptides, and molecules that co-exist a biological medium such as a cell extract. Accordingly, it may be desirable for many applications to further purify the labeled proteins or polypeptides of the invention prior to analysis by mass spectrometry. Any method known in the art for the separation of proteins and polypeptides may be used to accomplish this goal. Among these methods are one- and two-dimensional gel electrophoresis of proteins, varying dimensions of liquid chromatography of proteins or polypeptides, and HPLC, among other methods. If the label used is an affinity label, a resin comprising a moiety that binds to the affinity label may be used to isolate labeled proteins and polypeptides. For example, if biotin is used as a label, neutravidin beads may be used to isolate proteins and polypeptides resulting from proteolysis that have been labeled with peptide esters containing a biotin moiety.

In general, the data generated from mass spectrometry analyses (e.g., MS/MS peak lists) can be compared to sequence databases using computer programs available to the skilled artisan to determine the identity of labeled proteins. In some cases, labeled or modified peptides can be readily identified in MS/MS data by the presence of characteristic N-terminal modifications, such as characteristic di-peptide modifications (see, e.g., Example 1 and FIGS. 4 and 6).

In addition to identifying cellular proteins that undergo proteolysis in intact cells and tissues as a result of cellular signals, the skilled artisan will recognize that the methods of the present invention can be used to identify substrates of specific known proteases. For such applications, a cell or tissue extract can be made as described above and a known protease can be exogenously added to the extract. After an appropriate incubation period, the activity of the protease can be terminated and the labeling of newly exposed N-termini on polypeptides which have resulted from proteolysis can be performed as described above.

The methods of the present invention can also be used to identify proteins that are secreted by cells in response to cellular signals. For such applications, a cell can be stimulated with an agent of interest to stimulate protein secretion. In the case of tissue culture cells, after an appropriate incubation period, culture media from cells which have or have not been exposed to the agent can be isolated and the labeling of exposed N-termini on polypeptides which have been secreted into the culture media can be performed as described above.

EXAMPLES

The following examples are offered to illustrate, but not to limit the claimed invention.

Introduction

Apoptosis is a physiological process of significant importance in both health and disease. This form of programmed cell death regulates tissue differentiation and homeostasis in organisms by balancing new cell production with a corresponding level of cell death that, unlike necrosis, does not elicit an inflammatory response (Fadok et al., *Nature* 405, 85 (2000)). Since apoptotic turnover of cells is directly opposed to the uncontrolled growth of tumor cells, a strong link also exists between apoptosis and cancer. The end effect of most chemotherapeutic compounds in tumor cells is induction of apoptosis (Kaufmann et al., *Exp Cell Res* 256, 42 (2000)). The widespread intracellular proteolysis that is a hallmark of apoptosis is predominantly mediated by a family of aspartate-specific proteases termed caspases, but other proteases such as calpains (Gil-Parrado et al., *J Biol Chem* 277, 27217 (2002)), cathepsins (Michallet et al., *J Immunol* 172, 5405 (2004)), and HtrA2/OMI (Saelens et al., *Oncogene* 23, 2861 (2004)) can also be involved. Caspase proteolysis results in inactivation of prosurvival/antiapoptotic proteins and activation of antisurvival/proapoptotic proteins, and culminates in death and clearance of apoptotic cells (Luthi et al., *Cell Death Differ* 14, 641 (2007)). The regulation and execution of apoptosis is an immensely complex phenomenon. More than 350 human caspase protein substrates have so far been identified and new ones continue to be discovered (Luthi et al., *Cell Death Differ* 14, 641 (2007)). Adding to this complexity, the nature of the apoptotic response can vary in a stimulus-dependent and cell type-dependent manner that cannot always be predicted (Stepczynska et al., *Oncogene* 20, 1193 (2001); Wiegand et al., *Cell Death Differ* 8, 734 (July, 2001); Fulda et al., *Oncogene* 20, 1063 (2001); Scaffidi et al., *Embo J* 17, 1675 (1998)). Novel proteomic methods that permit global analysis of proteolysis during apoptosis have the potential to clarify some of this complexity.

Although proteases were initially characterized as mediators of nonspecific protein degradation, it is now accepted that many of these enzymes, like caspases, are highly selective and play pivotal roles in regulatory processes (Lopez-Otin et al., *Nat Rev Mol Cell Biol* 3, 509 (2002)). Such regulatory proteases function through specific and limited proteolysis to activate or inactivate proteins in various biochemical pathways. Since the function of regulatory proteases is largely determined by the events following cleavage of its physiological substrates, identification of these substrates is a crucial step for characterization of processes dependent on proteolysis. Proteolysis in cells or tissues is typically profiled by one- or two-dimensional gel electrophoresis (2DE), followed by identification of cleaved proteins by tandem mass spectrometry (MS/MS) (Gerner et al., *J Biol Chem* 275, 39018 (2000)), but this approach is limited in throughput and by the dynamic range of protein gels (Gygi et al., *Proc Natl Acad Sci USA* 97, 9390 (2000)). Proteomic studies of other post-translational modifications often make use of multidimensional chromatography in place of 2DE in conjunction with positive enrichment approaches for capture of phosphorylated polypeptides, glycosylated polypeptides, or polypeptides modified with ubiquitin-like proteins (Villen et al., *Proc Natl Acad Sci USA* 104, 1488 (2007); Vosseller et al., *Mol Cell Proteomics* 5, 923 (2006); Peng et al., *Nat Biotechnol* 21, 921 (2003)). In contrast, it is difficult to selectively capture the products of proteolysis, protein α-amines and α-carboxylates, and methods for selective enrichment of these moieties have only recently begun to be explored (Gevaert et al., *Nat Biotechnol* 21, 566 (2003); McDonald et al., *Nat Methods* 2, 955 (2005); Timmer et al., *Biochem J* 407, 41 (2007)).

We have developed a novel approach for monitoring proteolysis in complex samples that makes use of an engineered peptide ligase termed subtiligase to selectively label protein N-termini in complex samples. Subtiligase is a rationally designed mutant of the bacterial protease subtilisin BPN' that exhibits practically undetectable proteolytic activity, still hydrolyzes ester substrates as a normal protease would, but is a more efficient catalyst of aminolysis of peptide esters than normal proteases. Peptide ester turnover by subtiligase in the presence of free polypeptide α-amines results in ligation of the peptide portion of ester substrates onto polypeptide N-termini (Abrahmsen et al., *Biochemistry* 30, 4151 (1991)). Significantly, as a result of having been derived from a protease, subtiligase exhibits virtually absolute enzymatic specificity for acylation of protein N-terminal α-amines over lysine ε-amines (Chang et al., *Proc Natl Acad Sci USA* 91, 12544 (1994)). Furthermore, subtiligase exhibits broad specificity for the N-terminal amino acid of peptide nucleophiles, with N-terminal prolines and acidic residues serving as the poorest substrates (Abrahmsen et al., *Biochemistry* 30, 4151 (1991)). We have found that ligation of proteins in complex mixtures using subtiligase and labeled peptide esters, tryptic digestion, affinity purification of labeled N-terminal peptides, and identification of recovered peptides by tandem mass spectrometry permits cataloguing of protein N-termini in a given sample for corresponding protein identification and localization of proteolytic processing sites in cases where N-termini map to internal protein sequences (FIG. 6C).

Example 1

Methods and Materials

Expression and Purification of Subtiligase Variants: Expression constructs of subtiligase and related variants were prepared in the *B. subtilis/E. coli* shuttle vector pBS42 (ATCC) (Wells et al., *Nucleic Acids Res* 11, 7911 (1983)). These constructs were used to prepare recombinant subtiligase variants in *B. subtilis* strain 168 (ATCC). Subtiligase expression and purification was carried out essentially as described (Abrahmsen et al., *Biochemistry* 30, 4151 (1991)). The purified enzyme was stored at −80° C. in 100 mM BICINE, pH 8.0 and 10 mM DTT or TCEP.

Synthesis of Peptide Ester Substrates: Peptide glycolate ester substrates for subtiligase were prepared by solid-phase peptide synthesis using 9-fluorenylmethoxycarbonyl (Fmoc) chemistry as previously described (Braisted et al., *Methods Enzymol* 289, 298 (1997)). Peptides were purified using 10×50 mm XTerra Prep MS $C_{18}$ ODB colums on a Parallex Flex HPLC system (Biotage). Purity and identity of peptides was verified by LC/MS analysis using a 4.6×50 mm XTerra MS $C_{18}$ column on a 2795 HPLC (Waters) system equipped with a ZQ quadrupole MS detector (Waters).

Cell Culture, Induction of Apoptosis, and Cell Lysate Preparation: Jurkat clone E6-1 (ATCC) cells were grown in RPMI-1640 supplemented with 10% fetal bovine serum and were maintained between $1\times10^5$ and $2\times10^6$ cells/ml. For uninduced samples, cells were harvested at a density of $1\times10^6$ cells/ml. For apoptotic samples, cells at a density of $1\times10^6$ cells/ml were treated with etoposide (50 μM) for 12 hours prior to harvesting. Harvested cells were pelleted (0.1 to 1 billion), washed twice with phosphate buffered saline, and lysed in 1.0% Triton X-100, 100 mM BICINE pH 8.0, 100 μM Z-VAD-FMK, 100 μM E-64, 1 mM PMSF, 1 mM AEBSF, and 1 mM EDTA. Lysed cells were incubated at room temperature for 1 hour to allow complete inhibition of endogenous protease and esterase activity, and lysates were centrifuged at 21,000×g and 4° C. for 15 minutes to pellet insoluble material. Clarified supernatant was then immediately used in ligation reactions, typically at a concentration of $1\times10^8$ cells/ml, corresponding to a protein concentration of approximately 10 mg/ml as determined by Bradford assay. Higher lysate concentrations were also used, but this concentration was found to be the most favorable.

Ligation Reaction: Ligation reactions were carried out using stabiligase, a variant of subtiligase incorporating a set of additional mutations conferring increased protein stability under denaturing conditions (Chang et al., *Proc Natl Acad Sci USA* 91, 12544 (1994)). Stabiligase (1 μM), the biotinylated peptide ester TEVEST2 (1 mM), and DTT (2 mM) were added to either control or apoptotic cell lysate. Higher concentrations of peptide ester were also used, but a concentration of 1 mM was generally found to be the most favorable. The ligation reaction was then left to proceed at room temperature for 15 to 120 minutes, but 15 minutes were generally sufficient for completion of the reaction.

Sample Denaturation, Reduction, Alkylation, and Gel Filtration: The sample was denatured by direct addition of solid guanidine hydrochloride to a final concentration of 6 M, reduced by addition of neutralized TCEP (2 mM), heated at 95° C. for 15 minutes, cooled to room temperature, and alkylated by addition of iodoacetamide (6 mM) and incubation at room temperature in the dark for 1 hour. The alkylation reaction was then quenched by addition of DTT (10 mM), the sample was passed through a 0.8 μm filter, and subjected to gel filtration chromatography using a Superdex 30 16/60 column (GE Healthcare) on an ÄKTA FPLC system (GE Healthcare). The mobile phase was 100 mM BICINE pH 8.0, 200 mM NaCl, and 1 M guanidine hydrochloride. Fractions containing protein (corresponding to polypeptides ≥5 kDa) were collected and pooled for a final volume of approximately 30 ml.

Trypsinization, Capture of Biotinylated Peptides, and Recovery of Biotinylated Peptides: The gel filtered material was supplemented with $CaCl_2$ (20 mM) and digested with sequencing grade modified trypsin (100 µg, Promega) by incubation at 37° C. for 24 hours. Trypsinized samples were clarified by centrifugation, supplemented with benzamidine (500 mM), and Neutravidin agarose (250 µl bed volume, Pierce) was added for affinity capture of biotinylated N-terminal peptides. After 12 hours of gentle agitation, Neutravidin agarose resin was pelleted and washed with 100 mM BICINE pH 8.0 and AEBSF (1 mM), 100 mM BICINE pH 8.0, 5 M NaCl, and again with a few washes of 100 mM BICINE pH 8.0. More stringent washes using either 1 M or 5 M guanidine hydrochloride were also occasionally used. Captured peptides were then released from Neutravidin agarose resin by treatment with TEV protease (1 µM) in 100 mM BICINE pH 8.0 and DTT (1 mM). Recovered peptides were then concentrated and desalted using ZipTip$_{C18}$ pipette tips, or a $C_{18}$ Macrotrap (Michrom) trap column on a 2796 HPLC system (Waters). Solvent from desalted samples was removed using an EZ-2 Plus evaporator (GeneVac).

Sample Fractionation Using Strong Cation Exchange (SCX) Chromatography: In the case of larger scale experiments, samples were fractionated by SCX chromatography prior to LC/MS/MS analysis using a 2.1×200 mm PolySUL-FOETHYL Aspartamide column (The Nest Group) at a flow rate of 0.3 ml/min on a 2796 HPLC system (Waters). Buffer A consisted of 25 mM ammonium formate pH 2.8 and 30% acetonitrile, and buffer B consisted of 500 mM ammonium formate pH 2.8 and 30% acetonitrile. Approximately 25 fractions were collected during a 40 minute gradient block from 0% to 75% buffer B. Solvent from fractions was removed using an EZ-2 Plus evaporator (GeneVac), and remaining ammonium formate salt was removed by lyophilization. Some samples were also fractionated using a phosphate buffer and KCl salt system instead of an ammonium formate buffer system, in which case each fraction was subjected to automated desalting using a $C_{18}$ Microtrap (Michrom) trap column on a 2796 HPLC system (Waters) before solvent removal.

Nano-LC-ESI-Qq-TOF MS/MS Analysis: Desalted fractionated or unfractionated samples were separated with a 3-30% acetonitrile in 0.1% formic acid 1 hour gradient using a 75 µm×15 cm $C_{18}$ column (LC Packings) at a flow rate of 350 nl/min on a 1100 series HPLC system (Agilent). The LC eluent was coupled to a microion spray source attached to a QSTAR Pulsar or QSTAR XL mass spectrometer (Applied Biosystems/MDS Sciex). Peptides were analyzed in positive ion mode. MS spectra were acquired for 1 s. For each MS spectrum, either the single most intense or the two most intense multiply charged peaks were selected for generation of subsequent CID mass spectra, depending on the analysis method used. The CID collision energy was automatically adjusted based upon peptide charge and m/z ratio. A dynamic exclusion window was applied that prevented the same m/z from being selected for 3 min after its initial acquisition.

Interpretation of MS/MS Spectra: Data were analyzed using Analyst QS software (version 1.1), and MS/MS centroid peak lists were generated using the Mascot.d11 script (version 1.6b16). Data were searched against the Swiss-Prot human database initially using Mascot (Matrix Science), but later using Protein Prospector (University of California, San Francisco) as described herein. Initial peptide tolerance in MS and MS/MS modes were 200 ppm and 300 ppm, respectively. The digest protease specified was trypsin allowing for non-specific cleavage at N-termini in searches for labeled, N-terminal, semitryptic peptides, and trypsin allowing for non-specific cleavage at 0 N-termini in searches for contaminating, unlabeled, fully tryptic peptides. Up to either two, three or four missed cleavages were allowed, depending on the search. An N-terminal SY modification was specified as a fixed modification in searches for N-terminal peptides, but not in searches for unlabeled peptides. Cysteine carbamidomethylation was specified as a fixed modification and methionine oxidation was specified as a variable modification in all searches. High scoring peptide identifications from individual LC/MS/MS runs were then used to internally recalibrate MS parent ion m/z values within each run. Recalibrated data files were then searched again with an MS peptide tolerance of 50 ppm. Peptides with Protein Prospector peptide scores of ≥22 and peptide expectation values of ≤0.05 were considered positively identified. Peptides following aspartic acid in protein sequences were classified as P1 Asp peptides. False positive rates for peptide identifications were estimated by conducting searches using a concatenated database containing the original Swiss-Prot human database, as well as a version of each original database entry where the sequence had been randomized. The overall false positive rate for the 1072 N-terminal peptides identified was found to be 1.59% (17 false positive peptides), while the false positive rate for the 391 P1 Asp peptides identified was 0.00% (no false positive peptides). A representative sampling of SY-labeled peptide identifications, particularly those based on expectation values near 0.05, was also manually validated to ensure the validity of our automated interpretation criteria.

Labeling Serum: Two ml normal human serum (NHS) supplemented with 100 mM BICINE pH 8.0, 1 mM EDTA, 1 mM PMSF, and 10% DMSO is labeled with 1 mM TEVEST2 using 1 µM subtiligase at room temperature for 15 to 120 minutes, but 15 minutes were generally sufficient for completion of the reaction.

Example 2

Development of a Biotinylated Peptide Glycolate Ester

Figure 6A:
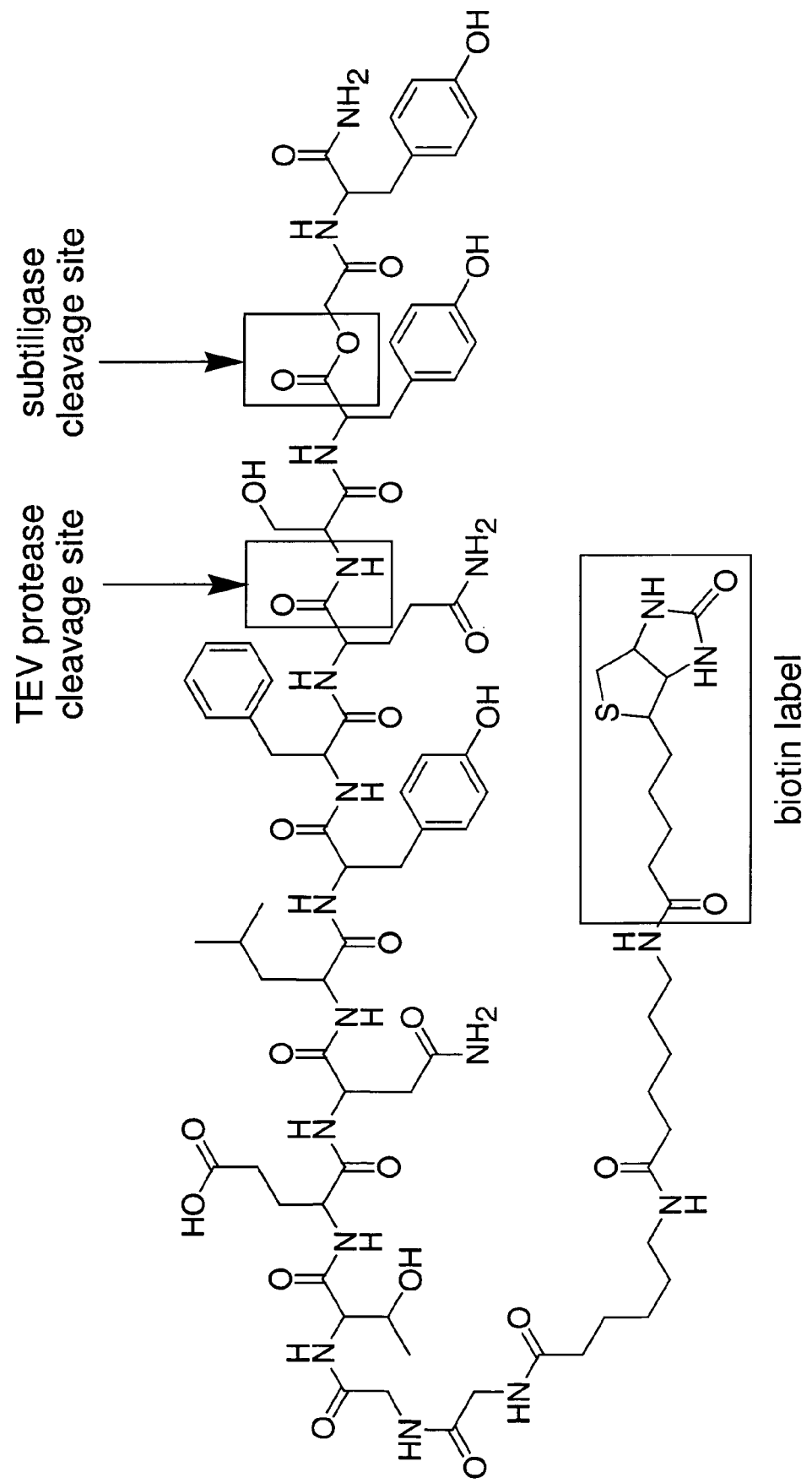
FIG. 6 shows a subtiligase-based method for positive selection of peptides corresponding to N-termini of proteins from complex mixtures. (A) Structure of the biotinylated peptide glycolate ester TEVEST2 (SEQ ID NO:19) used for proteomic experiments. After capture and cleavage by TEV protease, N-terminal peptides retain a characteristic Ser-Tyr tag. (B) Enzymatic labeling of proteins in Jurkat cell lysates using TEVEST2 and subtiligase. Lysates were treated either with TEVEST2 alone or with TEVEST2 and subtiligase, and samples were analyzed by SDS-PAGE followed by avidin blotting for detection of the biotin label. (C) Workflow for the biotinylation of protein N-temini in complex mixtures using TEVEST2 and subtiligase, trypsinization of labeled proteins for release of biotinylated N-terminal peptides, capture of these peptides using immobilized avidin, recovery of captured peptides using TEV protease, optional fractionation of samples by strong cation exchange chromatography, and LC/MS/MS analysis for identification of corresponding proteins and cleavage sites.
Figure 6B:
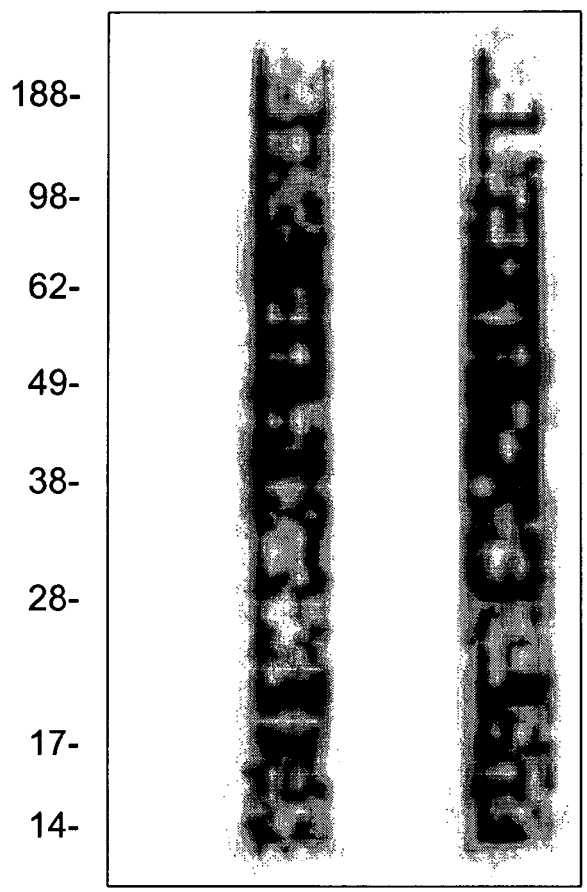
Figure 6C:
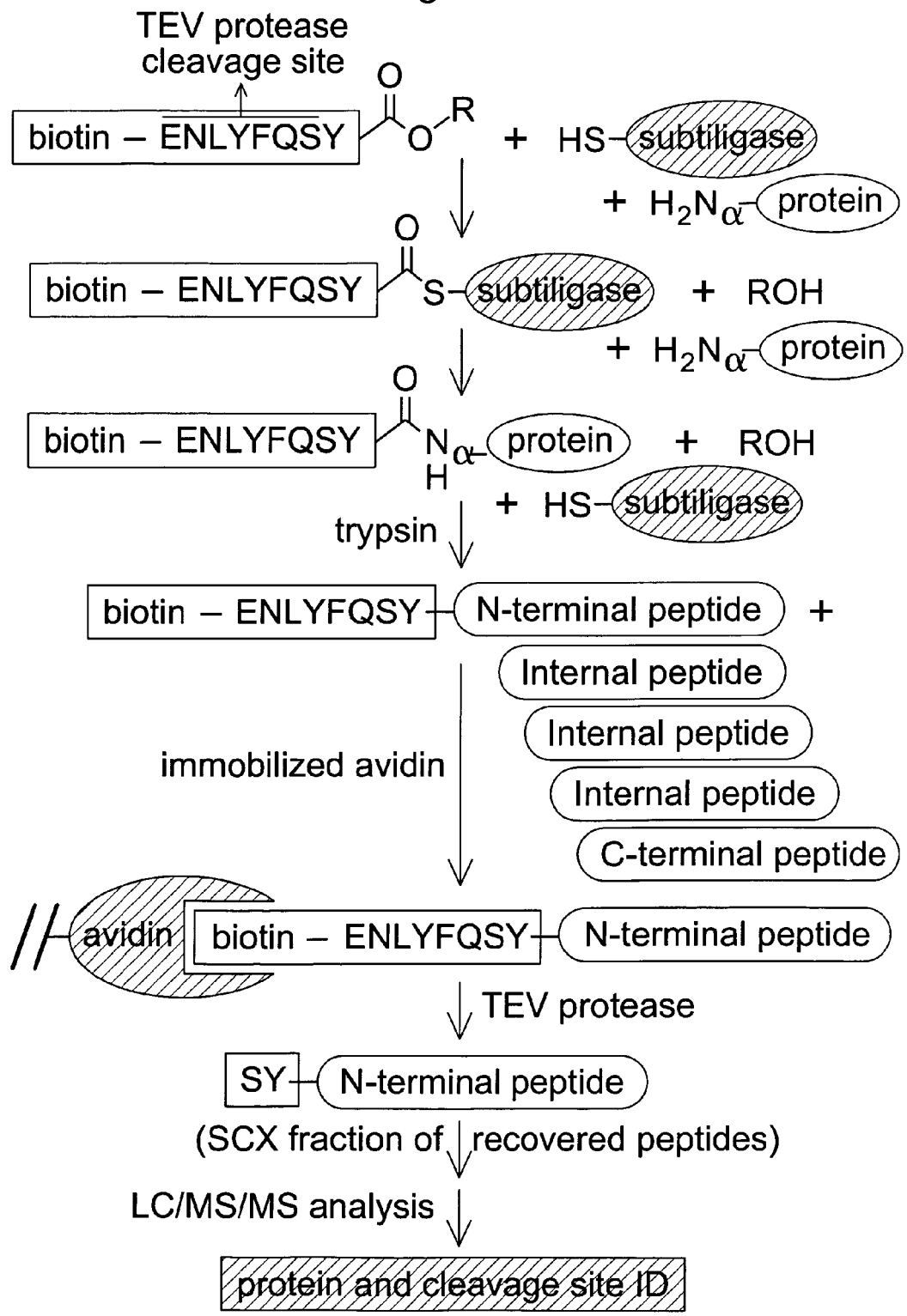

A crucial first step in the development of the subtiligase-based proteomic method described herein was development of the biotinylated peptide glycolate ester TEVEST2 (FIG. 6A). Peptide glycolate esters have previously been demonstrated to function as efficient subtiligase substrates (Abrahmsen et al., *Biochemistry* 30, 4151 (1991)). Tyrosine was selected as the residue to be esterified because aromatic residues are particularly favored by subtiligase at the position preceding the scissile ester bond. Biotin was selected as the label because its essentially irreversible binding to avidins makes it a powerful handle for affinity purification of labeled polypeptides, provided a good strategy is used for efficient recovery of biotinylated material from avidin affinity media. TEVEST2 incorporates the tobacco etch virus (TEV) protease cleavage site ENLTFQ-S (SEQ ID NO:14) between biotin and the site of ligation for this purpose. TEV protease exhibits highly stringent specificity and there is extensive precedent for use of TEV protease cleavage sites in the recovery of purified fusion proteins from affinity media (Rigaut et al., *Nat Biotechnol* 17, 1030 (1999)). Treatment of Jurkat cell lysates either with TEVEST2 alone, or with TEVEST2 in conjunction with subtiligase, followed by SDS-PAGE and avidin blot analysis demonstrates that labeling of proteins in celllysates with the biotinylated peptide ester is dependent on subtiligase (FIG. 6B). Use of TEVEST2 for subtiligase-mediated labeling of complex protein mixtures enables affinity purification of peptides for LC/MS/MS analysis that are N-terminally modified with a SY dipeptide, an advantageous hallmark to distinguish ligated peptides from other contaminating unligated peptides (FIG. 6C).

Example 3

Use of Subtiligase to Label the N-termini of Proteins

Figure 5B:
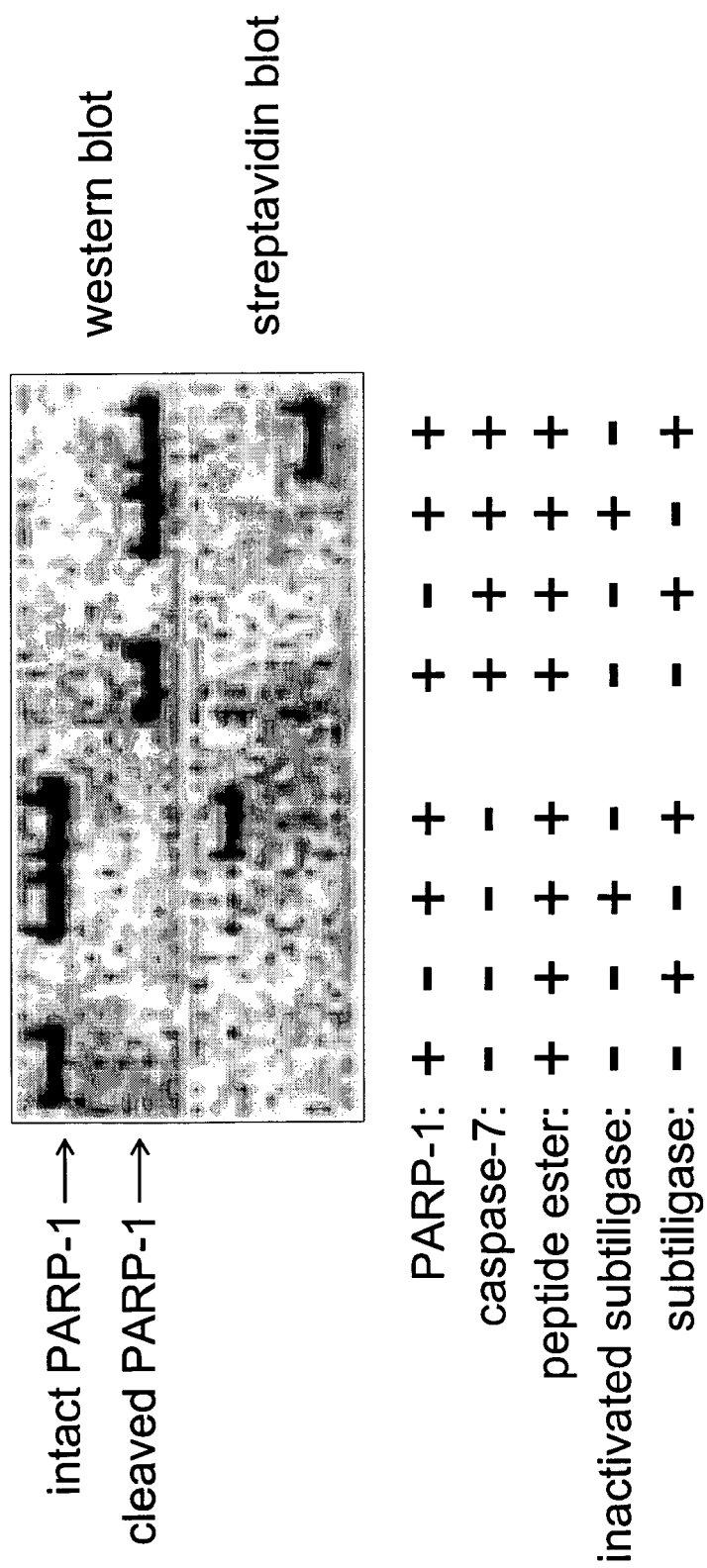

The enzyme subtiligase, an engineered variant of subtilisin, was originally developed for the synthesis and semi-synthesis of proteins. We show in this Example that subtiligase will efficiently ligate peptide-esters exclusively onto the N-terminus of proteins using the model substrates recombinant human growth hormone (rhGH) and recombinant PARP-1. As shown in FIG. 5A, when recombinant human growth hormone (rhGH) was treated with subtiligase and BIOEST1 and the reaction was analyzed by ESI-TOF mass spectrometry, a single modification event per protein (+870±5 Da) was observed, which indicated that ligation occurs at the N-terminus and not at surface exposed lysine residues. As another example, FIG. 5B shows a western and avidin blotting experiment that reveals that treatment of recombinant PARP-1 with subtiligase and BIOEST1 leads to ligation and biotinylation of this recombinant protein, whether in intact form (113 kDa) or after processing with recombinant caspase-7 (89 kDa).

No other enzyme, either designed or natural, has been reported which is better suited for N-terminomics applications. Subtiligase shows excellent activity and broad specificity for the incoming α-amine and thus is ideally suited for labeling newly proteolyzed substrates. The labels contain a biotin handle and TEV protease release site allowing the proteolysis products to be isolated and enriched over non-cleaved proteins. In the case of proteolysis, this is a major advantage over other chemical degradomics approaches because low abundance proteolysis events can be enriched by affinity chromatography. Using subtiligase in this new way, we can identify all the proteins in cells that are cleaved by proteases of interest or discover proteins cleaved by proteases in response to cellular signaling events.

Example 4

Analysis of Endogenous N-Termini of Unstimulated Jurkat Cells

Leukemias account for the largest number of childhood cancer cases in the United States and are the primary cause of cancer related mortality of children. A strong link exists between apoptosis and cancer because apoptotic turnover of cells is directly opposed to the uncontrolled growth of tumor cells. Most established anticancer agents now in use function by inducing apoptosis. A distinct molecular feature of apoptosis is widespread but controlled cellular proteolysis, which is predominantly mediated by the caspase family of cysteine proteases. Many of the targets of caspase proteolysis function as anti-apoptotic factors. For example, RNA interference (siRNA) of a number of known caspase substrates induces apoptosis or tumor growth inhibition (e.g. Bcl-2, XIAP, BCR-Abl, focal adhesion kinase, MDM2, β-catenin, and heterogeneous nuclear ribonucleoproteins A1 and A2). In a number of cases, the targets of anticancer agents have been shown to be targets of caspase proteolysis during apoptosis. These include topoisomerases I and II, the target of etoposide; the prosurvival kinases Akt/PKB and Mek-1; anti-apoptotic proteins Bcl-2, XIAP, PARP, and MDM2; cell cycle proteins cdk2 and cyclins A and E. Thus, the study of apoptotic pathways has important ramifications for the development of new therapies for treatment of cancer. In particular, identification of new targets of proteolysis in apoptosis may lead to the discovery of anti-apoptotic or prosurvival factors, and thus identify novel targets for apoptosis-based cancer therapies.

Figure 7A:
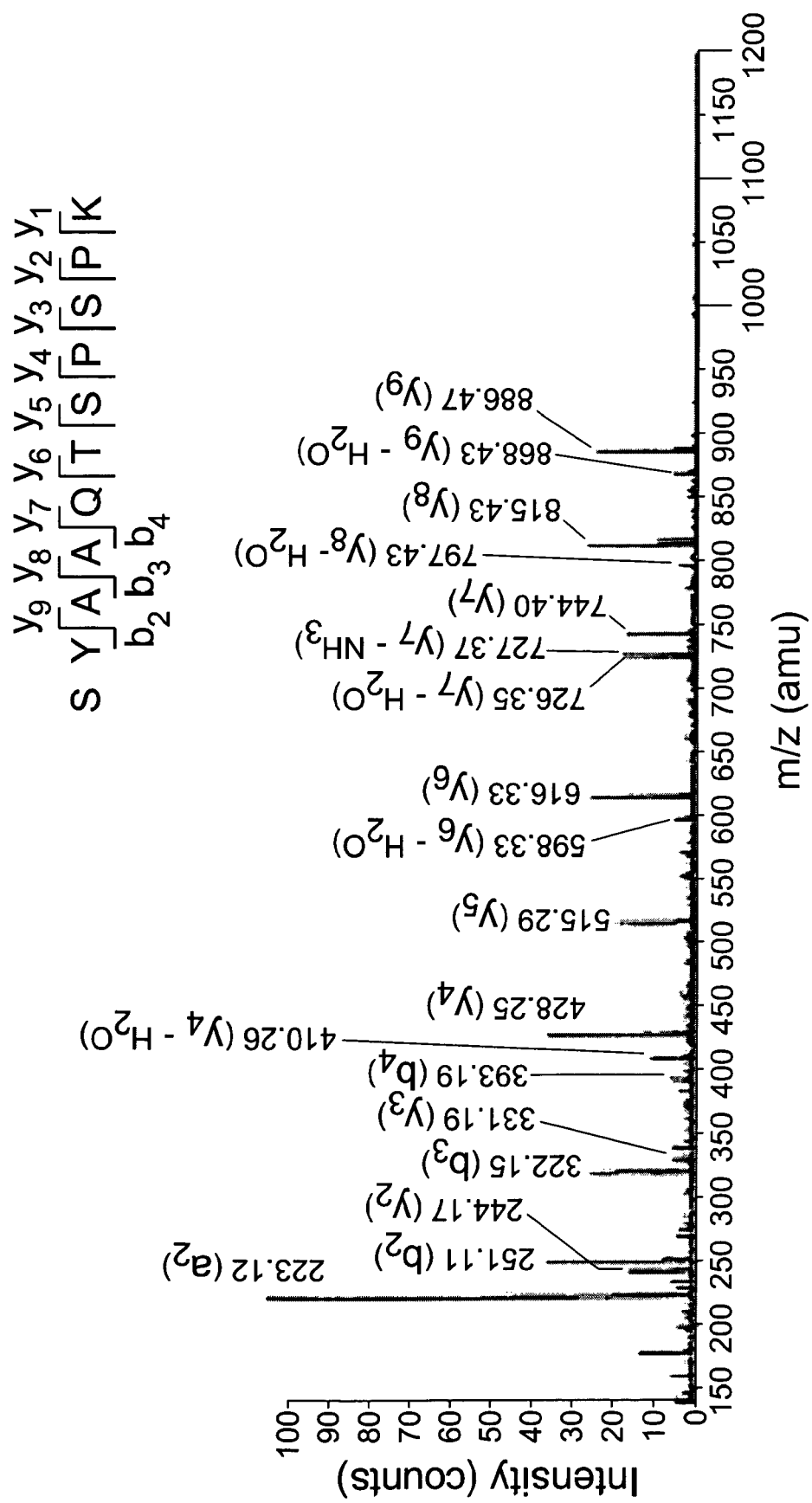
FIG. 7 shows recovery of true endogenous N-termini from unstimulated Jurkat cells. (A) Labeling of the N-terminus created in ATP synthase β chain (Swiss-Prot accession # P06576) following mitochondrial transit peptide processing. The MS/MS spectrum corresponds to semitryptic peptide AAQTSPSPK (SEQ ID NO:2) modified at its α-amine with the dipeptide SY. Sequence: SYAAQTSPSPK (SEQ ID NO:20). The N-terminal alanine of this peptide corresponds to residue 47 in the protein, and the mitochondrial transit peptide of ATP synthase β chain is annotated in Swiss-Prot as residues 1-47 (by similarity). The $a_2$ and $b_2$ ions are characteristic hallmarks of a ligated, N-terminal SY-bearing peptide. (B) Classification of the 90 N-termini identified in a single unfractionated sample from unstimulated Jurkat cells. 54% of these are annotated as indicated in Swiss-Prot, and 72% of the remaining N-termini are found within the first 50 residues of corresponding proteins, indicating that these also likely arise from endogenous N-terminal processing events (i.e. signal peptidase and dipeptidase activity). (C) Frequency of N-terminal amino acids in the 90 N-termini identified in unstimulated Jurkat cells indicates that approximately 90% are either methionine or a small residue, obeying the N-end rule for protein cellular stability. (D) Frequency of putative P1 amino acids (residues in the protein sequence preceding the first amino acid of each N-terminus) for the 90 N-termini identified in unstimulated Jurkat cells indicates that endogenous proteolytic events occur most commonly following methionine, as well as phenylalanine, leucine, and tyrosine. "–" represents lack of putative P1 residue (i.e. the identified N-terminal peptide was the initiator methionine).
Figure 7B:
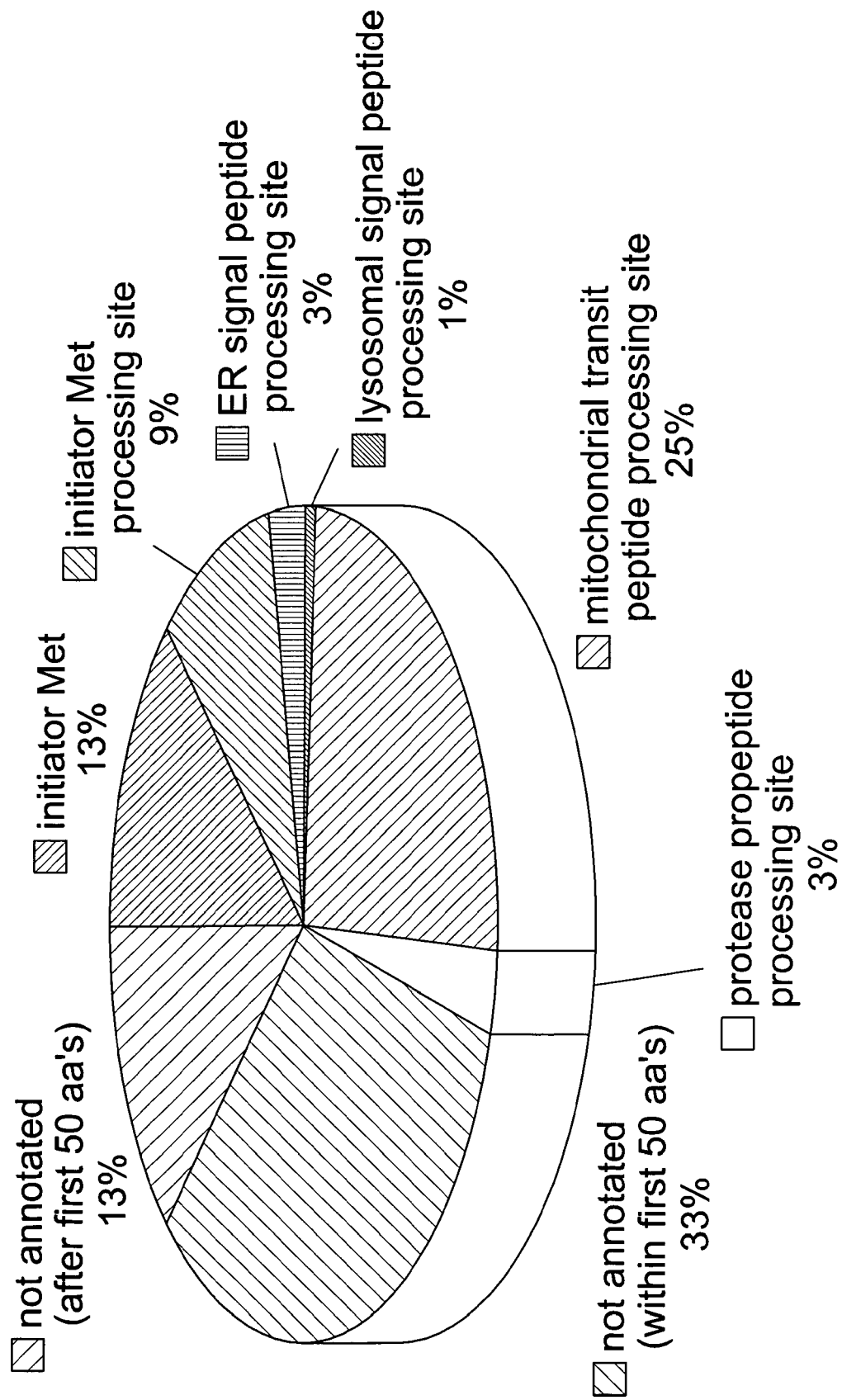
Figure 7C:
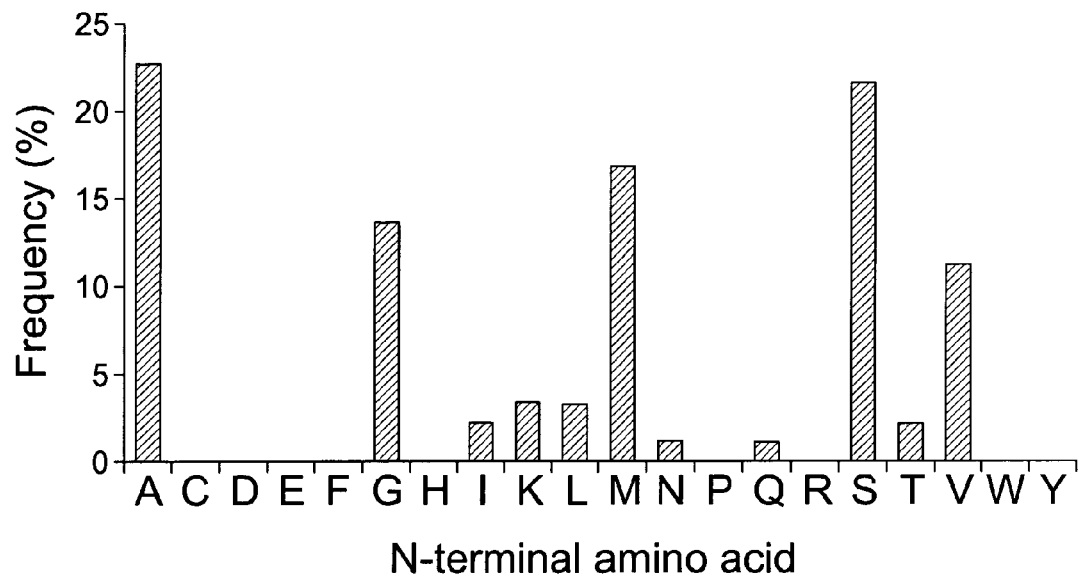
Figure 7D:
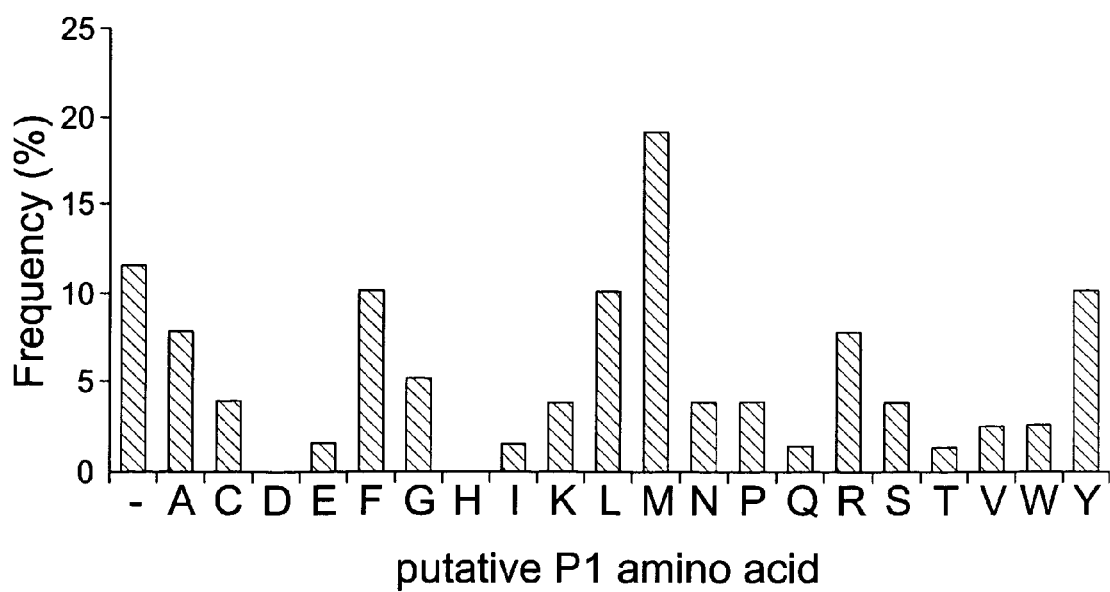

In this example, we applied the methods described herein to the analysis of endogenous N-termini of unstimulated Jurkat cells as a first step in studying apoptosis. A total of 104 peptides bearing an N-terminal SY dipeptide modification were identified using a sample that was not subjected to SCX fractionation. These peptides correspond to 88 unique N-termini and 2 additional N-termini that exist in more than one homologous protein. In turn, these N-termini correspond to 83 unique proteins and 2 additional proteins that cannot be distinguished from homologs. The SY-labeled peptide corresponding to the N-terminus created in ATP synthase β chain following mitochondrial transit peptide processing is an example of the peptides recovered (FIG. 7A). Swiss-Prot annotation reveals that 54% of the identified peptides are true N-termini, including initiator methionines and sites of methionine aminopeptidase processing, ER signal peptide processing, lysosomal signal peptide processing, mitochondrial transit peptide processing, and protease propeptide processing (FIG. 7B). Additionally, 72% of the remaining N-termini are found within the first 50 residues of corresponding proteins, indicating that these also likely arise from endogenous N-terminal processing by signal peptidases and dipeptidases. The frequency of first amino acids in the identified N-termini indicates that approximately 90% obeying the N-end rule for protein cellular stability, again lending support to the notion that the recovered peptides represent true endogenous N-termini (FIG. 7C). The frequency of putative P1 amino acids (residues in the protein sequence preceding the first amino acid of each N-terminus) for the identified N-termini indicates that endogenous proteolytic events in unstimulated Jurkats occur most commonly following methionine, as well as phenylalanine, leucine, and tyrosine (FIG. 7D).

Example 5

Analysis of Apoptosis in Etoposide Treated Jurkat Cells

The acute lymphocytic leukemia cell line Jurkat has historically served as a common model system for the study of apoptosis (Gerner et al., *J Biol Chem* 275, 39018 (2000)). We have utilized Jurkat cells stimulated with the chemotherapeutic etoposide in our proteomic studies. Three separate large scale proteomic experiments with etoposide-treated Jurkat cells were carried in which samples were subjected to SCX fractionation prior to LC/MS/MS analysis in order to achieve greater proteomic coverage. The peptides, N-termini, and proteins identified in these experiments were grouped into datasets 1, 2, and 3, respectively. Peptides, N-termini, and proteins identified in any other smaller scale experiments we have carried out with etoposide-treated Jurkat cells were grouped into dataset 4. Datasets 1, 2, 3, and 4 represent the identification of, respectively, 489, 411, 401, and 550 peptides bearing an N-terminal SY dipeptide modification. In total, our studies resulted in identification of 1072 peptides bearing an N-terminal SY dipeptide modification, with an overall false positive rate for peptide identifications of 1.59% as determined using a target-decoy search strategy (Elias et al., *Nat Methods* 4, 207 (2007)). These peptides correspond to 849 unique N-termini and 39 additional N-termini that exist in more than one homologous protein. In turn, these N-termini correspond to 646 unique proteins and 32 additional proteins that cannot be distinguished from homologs.

Figure 8A:
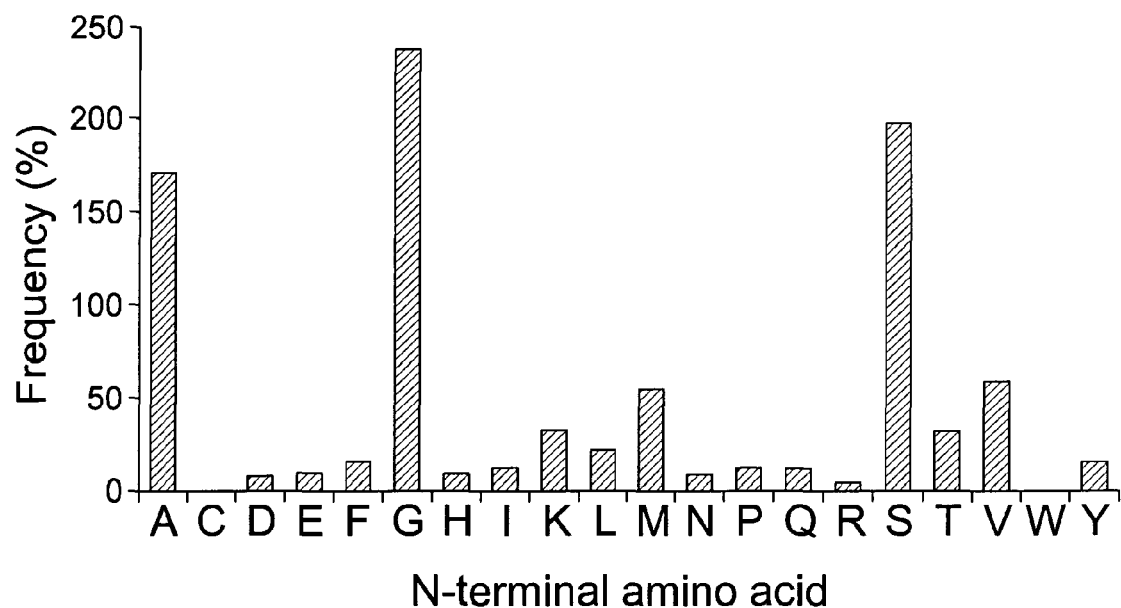
FIG. 8 shows recovery of putative caspase-derived N-termini from etoposide-stimulated apoptotic Jurkat cells. (A) Frequency of N-terminal amino acids in the 888 N-termini identified in all combined experiments using etoposide-stimulated apoptotic Jurkat cells indicates accordance with the strict specificity of caspases for alanine, glycine, or serine at P1'. (B) Frequency of putative P1 amino acids (residues in the protein sequence preceding the first amino acid of each N-terminus) for the 888 N-termini identified in etoposide-stimulated apoptotic Jurkat cells indicates the striking abundance of proteolytic events following aspartic acid, in accordance with the strict specificity of caspases for this residue at P1. "–" represents lack of putative P1 residue (i.e. the identified N-terminal peptide was the initiator methionine). (C) Labeling of the N-terminus created in MEK1 (Swiss-Prot accession # Q02750) following processing after aspartic acid residue 16. The MS/MS spectrum corresponds to semitryptic peptide GSAVNGTSSAETNLEALQK (SEQ ID NO:3) modified at its α-amine with the dipeptide SY. Sequence: SYGSAVNGTSSAETNLEALQK (SEQ ID NO:21). MEK1 is a known caspase substrate, but the putative caspase cleavage site corresponding to this N-terminal peptide, PAPD(16)-
Figure 8B:
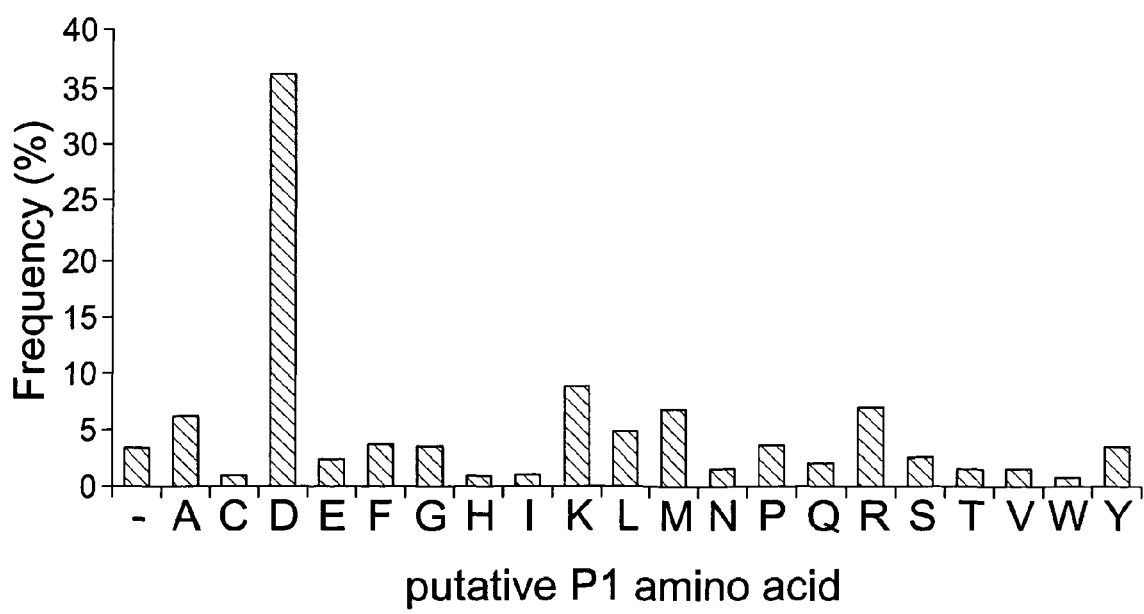
Figure 8C:
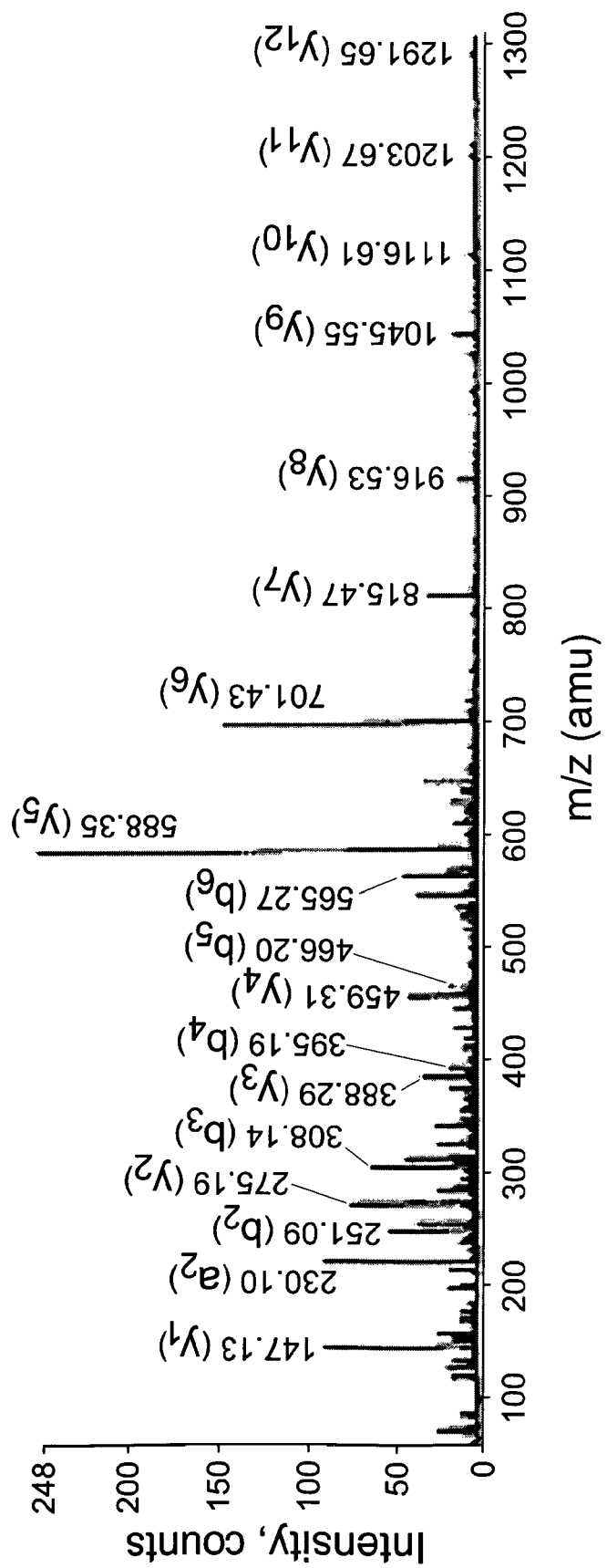

The frequency of first amino acids in all N-termini identified in apoptotic Jurkat cells indicates that, although these still obey the N-end rule for protein cellular stability, the profile observed in unstimulated cells appears to be suppressed by a striking increase in frequency of alanine, glycine, and serine residues (FIG. 8A). This is entirely consistent with the role of caspases in apoptosis, which exhibit strict specificity for alanine, glycine, and serine at P1' (position following the scissile bond in proteolysis) (Stennicke et al., *Biochem J* 350 Pt 2, 563 (2000)). The frequency of putative P1 amino acids (residues in the protein sequence preceding the first amino acid of each N-terminus) for all N-termini identified in apoptotic Jurkat cells indicates the striking abundance of proteolytic events following aspartic acid (FIG. 8B). This is again entirely consistent with the role of caspases in apoptosis, which exhibit strict specificity for aspartic acid at P1 (Stennicke et al., *Biochem J* 350 Pt 2, 563 (2000)). Although the role of caspases in apoptosis is well established, this data highlight the sheer extent to which caspases (or caspase-like proteases cleaving after aspartic acid) are responsible for the proteolysis that occurs during apoptosis. An example of a putatively caspase-derived peptide identified in apoptotic Jurkat cells is the peptide GSAVNGTSSAETNLEALQK (SEQ ID NO:15) from the dual specificity kinase MEK1, modified at its N-terminus with the dipeptide SY (FIG. 8C). MEK1 is known to be cleaved by caspases during apoptosis (McGuire et al., *J Biol Chem* 276, 26365 (2001)), but the putative caspase cleavage site corresponding to this N-terminal peptide, PAPD(16)-GSAV (SEQ ID NO:16) has not been previously reported. Interestingly, this cleavage site is only 8 residues away from the site where the metalloprotease anthrax lethal factor cleaves and inactivates MEK1, KPTP(8)-IQLN (SEQ ID NO:17) (Duesbery et al., *Science* 280, 734 (1998)).

Datasets 1, 2, 3, and 4 represent the identification of, respectively, 190, 141, 125, and 160 peptides bearing an N-terminal SY dipeptide modification that also follow aspartic acid in corresponding protein sequences. These P1 Asp peptides were deemed to be putative caspase-derived N-termini if the aspartic acid occurred at or following protein residue 4. In total, our studies resulted in identification of 391 P1 Asp peptides bearing an N-terminal SY dipeptide modification, with an overall false positive rate for P1 Asp peptide identifications of 0.00%. These peptides correspond to 309 unique N-termini and 9 additional N-termini that exist in more than one homologous protein. In turn, these N-termini correspond to 272 unique putative caspase substrates and 7 additional putative caspase substrates that cannot be distinguished from homologs. Although the overlap between unique putative caspase substrates from all four datasets is significant, it is not complete, indicating that the 272 putative caspase substrate summation from all datasets is likely only a partial sampling of available caspase substrates (FIG. 8D).

Figure 9A:
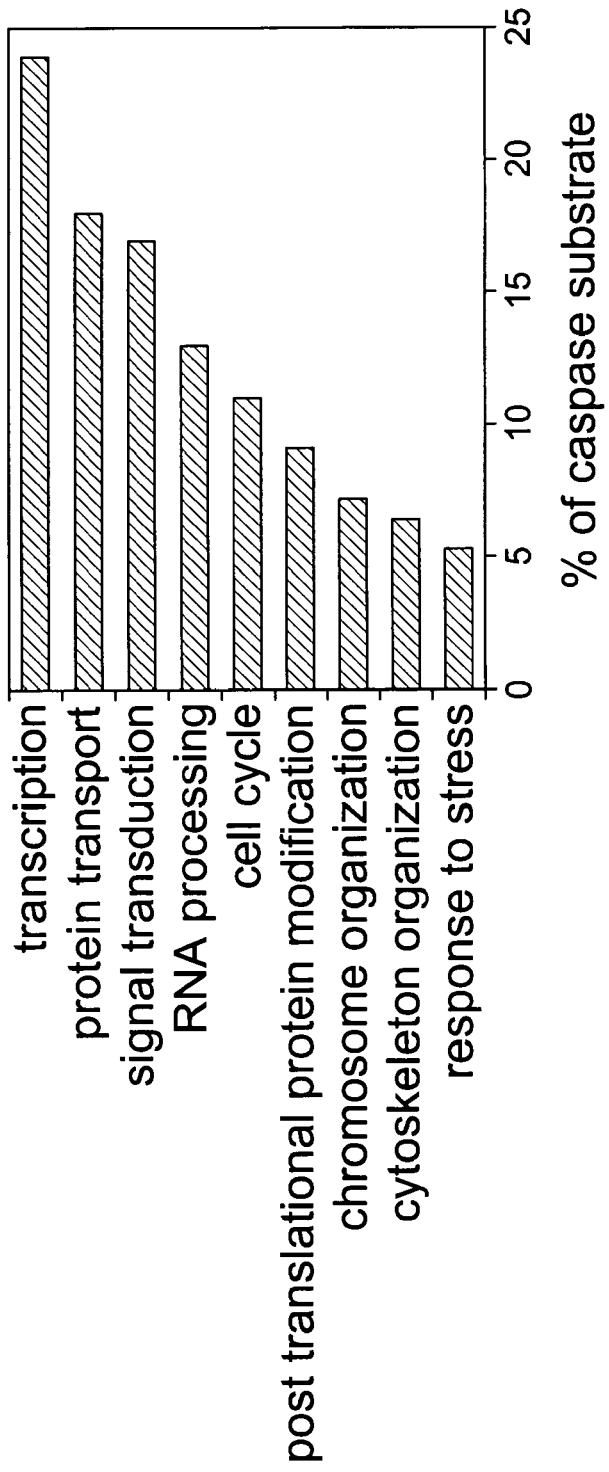
Figure 9D:
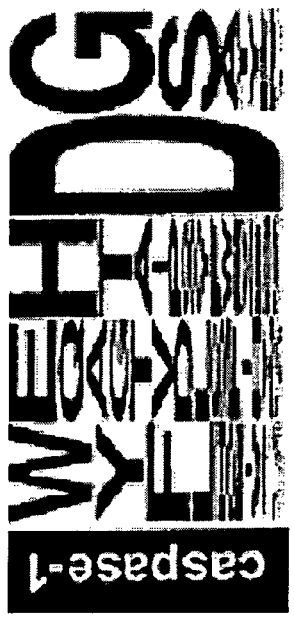
Figure 9E:
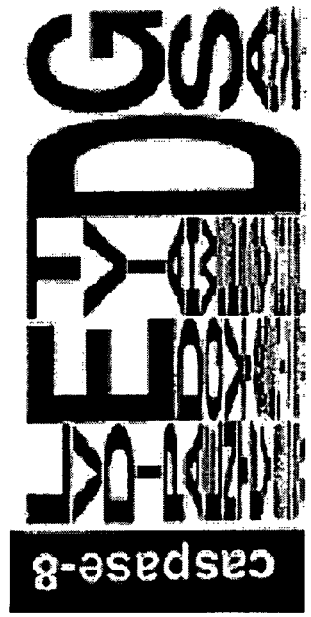
Figure 9F:
Figure 9B:
Figure 9C:
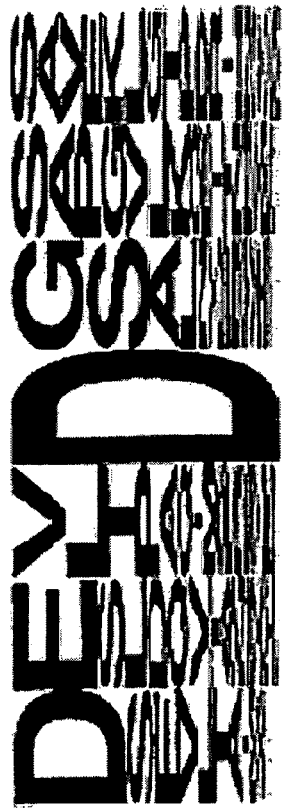

Classification of the identified caspase substrates using Gene Ontology terms (www.geneontology.org) indicates that these proteins fall into a wide range of functional classes that are all consistent with the biology of apoptosis (FIG. 9A). The distribution of amino acids in the 318 identified putative caspase cleavage sites indicates that the most common caspase-like activity in apoptotic cells is an executioner caspase-like activity corresponding to a DEVD-G/S/A (SEQ ID NO:18) cleavage site (FIG. 9B). This is presumably attributable to caspases-3, -6, and -7, instead of other caspases that are known to exhibit inflammatory caspase- and initiator caspase-like substrate specificity (FIGS. 9D, 9E, and 9F) (Thornberry et al., *J Biol Chem* 272, 17907 (1997)). Nevertheless, data from caspase substrate specificity studies does not fully account for the distribution of residues observed in the P1 Asp cleavage sites we have identified. For example, the abundance of serine and threonine residues at P4 and P3 cannot be explained by such studies. This discrepancy could be explained by the fact that protein substrate-caspase interactions may be dependent on specificity determinants that are distal to the active site and are not evaluated in typical studies with synthetic protease substrates. Such "exosite" determinants may exist to, for example, allow overlap between caspase cleavage sites and phosphorylation sites, which in turn allows for opposing effects of proteolysis and phosphorylation in the cellular balance of life and death (Tozser et al., *Biochem J* 372, 137 (2003)). Strikingly, the distribution of amino acids in the putative capase cleavage sites identified in our work is almost identical to that of previously reported cleavage sites in known caspase substrates (FIG. 9C) (Luthi et al., *Cell Death Differ* 14, 641 (2007)), including the prevalence of potentially phosphorylatable serine residues at P4 and P3. The similarity between the sequence logos of FIGS. 9B and 9C is a compelling argument for the notion that the proteins we have deemed to be putative caspase substrates are in fact true endogenous caspase substrates.

Example 6

Identification of N-termini of Serum Proteins with Subtiligase

Using the methods described in Example 1, labeling of proteins in serum was performed. As a result of this study, 79 nonredundant peptides were identified in a single LC/MS/MS run, corresponding to 34 unique proteins. 68% of the peptides corresponded to an annotated N-terminus resulting from signal cleavage or other known functional proteolytic processing. The 32% of N-terminal peptides with unknown origin indicated the potential of this technique to identify previously unknown posttranslational modifications in serum proteins. The abundances of identified proteins spanned five orders of magnitude, from the processed N-terminus of serum albumin (~20 mg/ml) to insulin-like growth factor II (~500 ng/ml). Low-abundance serum proteins could be identified despite no effort being made to deplete high-abundance proteins prior to analysis, illustrating the power of this labeling technique to partially neutralize dynamic range problems that confound serum proteomics. These results were obtained without prefractionation of the labeled serum peptides. Significantly improved depth of coverage can be obtained with SCX fractionation.

TABLE 2

Representative N-terminal peptides identified

| Protein | Cleavage after residue # | Annotation |
| --- | --- | --- |
| von Willebrand factor | 764 | Processed precursor |
| Factor V | 1047 | Cleavage by thrombin |
| Insulin-like growth factor II | 24 | Signal peptide |
| Antithrombin III | 32 | Signal peptide |
| Antithrombin III | 425 | Serpin reactive site |
| Hepatocyte growth | 372 | Processed precursor |

TABLE 2-continued

Representative N-terminal peptides identified

| Protein | Cleavage after residue # | Annotation |
|---|---|---|
| factor activator Complement C4 | 678 | Processed precursor; α-chain N-terminus |
| Complement C4 | 956 | C4d fragment; cleavage by Factor I |
| Complement C4 | 1352 | Not annotated |
| Complement C4 | 1453 | Processed precursor; γ-chain N-terminus |
| Thrombin | 327 | Light chain N-terminus; cleaved by factor Xa |

Conclusion

Highly selective methods for labeling products of proteolysis for cellular degradomics have not been previously developed. Thus, proteolysis in biology is typically studied by in vitro methods examining a single protease at a time, often with a single protein substrate at a time, and under artificial conditions. Perhaps the most serious limitation of these in vitro approaches is a propensity to yield physiologically irrelevant results. In vivo, proteases interact with substrates in the context of a system of other biomolecules that can lead to inhibition, activation, compensation, and temporal or spatial separation. A global and systems-level approach to profile proteolytic events will yield the most physiologically relevant results. Modern proteomic methods are theoretically well suited for the global study of proteolysis in complex mixtures. Profiling of proteolysis in cells or tissues is often carried out using one- or two-dimensional gel electrophoresis (2DGE) followed by tandem mass spectrometric identification of cleaved proteins. However, a significant limitation of this approach is the inherent limited dynamic range of protein gel electrophoresis that results from limited sample loading capacity as previously noted in the art. This greatly reduces the utility of 2DGE for degradomics research.

Furthermore, the cleaved products of proteolysis blend with the entire proteome and cannot be enriched from the background of endogenous proteins. Proteolysis generates new α-amino and α-carboxy termini that have the potential to be tagged. However, prior chemical approaches cannot label them with sufficient selectivity over other carboxyl and amino containing amino acids to adequately distinguish them.

Recently, there has been a surge in gel-free proteomic methods that make use of multidimensional chromatography in place of 2DGE, often also making use of isotope-coding strategies to quantify, at the mass spectrometric step, changes in protein levels in experimental samples relative to control samples. These methods usually employ "bottom-up" proteomic approaches as opposed to "top-down" approaches. In "bottom-up" approaches, complex mixtures of proteins are extensively proteolyzed to yield peptides, which are first separated using multiple dimensions of chromatography, and then analyzed by tandem mass spectrometry for identification of corresponding proteins. In "top-down" approaches, entire proteins are analyzed by mass spectrometry using emerging technologies such as electron capture dissociation (ECD), which enable fragmentation of entire proteins in the mass spectrometer for protein identification. Although top-down approaches are rapidly evolving, they currently do not offer the proteomic coverage and high-throughput offered by bottom-up approaches for the analysis of thousands of species from complex biochemical mixtures.

Another method proposed for the forward degradomics analysis of proteolysis that occurs during apoptosis, referred to as combined fractional diagonal chromatography (COFRADIC), is based on a negative selection for isolation of N-termini by acetylation. However, this method precludes positive selection and enrichment and thus reduces sensitivity. Moreover, all N-termini and lysine residues are chemically acetylated in this method, preventing the use of powerful iTRAQ reagents for isotope-coding. Finally, the COFRADIC method selects for, and is thus subject to high background arising from, N-termini that are endogenously acetylated, which represents approximately 80% of proteins in mammalian cells (Van Damme et al., 2005, *Nature Methods* 2, 771-777).

The methods of the present invention overcome many of the problems in the art by use of a completely selective labeling of α-amines with biotinylated tags that provide for positive selection, enrichment, and products that are amenable to mass spectrometry-based quantitation using isotope-coding techniques.

Moreover, it has been estimated that approximately 80% of eukaryotic proteins are N-terminally acetylated as a post-translational modification (Brown et al., *J Biol Chem* 251, 1009 (1976)). Greater sensitivity over background can thus be achieved through N-terminal instead of C-terminal labeling of proteolysis products, but to be effective, any such labeling approach must exhibit great selectivity for terminal α-amines over lysine ε-amines. This challenge is compounded by the fact that protein ε-amines are more abundant than α-amines, and modest levels of lysine cross-reactivity can potentially add up to a significant undesired background. We have overcome this challenge using an enzymological approach that employs the rationally designed protein ligase subtiligase in developing a novel and effective method for global profiling of proteolysis in complex mixtures. Alternative N-terminal peptide purification strategies have recently been reported that are all based on chemical derivatization approaches. Gevaert et al. and McDonald et al. have reported similar methods for negative selection of N-terminal peptides, while Timmer et al. have reported another approach for positive selection of N-terminal peptides (Gevaert et al., *Nat Biotechnol* 21, 566 (2003); McDonald et al., *Nat Methods* 2, 955 (2005); Timmer et al., *Biochem J* 407, 41 (2007)). All of these chemical approaches rely on two consecutive and quasi-orthogonal derivatization steps, the first for lysine ε-amines, and the second for terminal α-amines. The methods described herein offer the advantage of a positive selection approach that achieves selectivity for terminal α-amines in one single labeling step instead of two interdependent ones, and thus represents a significant advance over these previously described methods.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method for globally profiling polypeptides in complex mixtures, the method comprising the steps of:

contacting at least one complex mixture with a labeling agent that reacts with α-amino groups of a plurality of polypeptides in the complex mixture, wherein the at least one complex mixture is a biological sample, wherein the biological sample is a cell extract, a cell, a cell culture medium or a bodily fluid, and wherein the labeling agent is subtiligase and a substrate, thereby specifically labeling the α-amino groups of polypeptides in a complex mixture; and detecting the plurality of polypeptides that are labeled at α-amino groups in the complex mixture, thereby globally profiling the polypeptides that are present in the complex mixture.

2. The method of claim 1, wherein the substrate comprises a peptide ester with a subtiligase cleavage site.

3. The method of claim 2, wherein the peptide ester further comprises a label, wherein the label is selected from the group consisting of a radioisotope, a stable isotope, a fluorophore, electron dense metals, biotin, DNA, RNA, and antibody epitopes.

4. The method of claim 2, wherein the substrate further comprises a cleavable linker.

5. The method of claim 4, wherein the cleavable linker is cleaved by TEV protease.

6. The method of claim 4, wherein the cleavable linker comprises the amino acid sequence ENLYFQSY (SEQ ID NO:1).

7. The method of claim 2, wherein the peptide ester is TEVEST2.

8. The method of claim 1, wherein the detecting is performed using mass spectrometry, two dimensional electrophoresis, or chromatography.

9. The method of claim 1, wherein the cell extract is prepared from a cell treated with an agent that provides a cellular signal to stimulate proteolysis, or from a cell treated with an apoptotic agent.

10. The method of claim 9, wherein the apoptotic agent is a small molecule, a polypeptide or a chemotherapeutic drug.

11. The method of claim 1, wherein a first cell extract is prepared from a cell treated with an agent that provides a cellular signal to stimulate proteolysis and a second cell extract is prepared from a control cell, wherein a first cell extract is prepared from a cell treated with an apoptotic agent and a second cell extract is prepared from a control cell, or wherein a first cell extract is a membrane extract prepared from a cancer cell and a second cell extract is a membrane extract prepared from a normal cell.

12. The method of claim 10, wherein the apoptotic agent is a chemotherapeutic drug.

13. The method of claim 12, wherein the chemotherapeutic drug is selected from the group consisting of etoposide, adriamycin, cisplatin, taxol, bleomycin, CDDP, methotrexate, vincristine, and hydroxyurea.

14. The method of claim 12, wherein the chemotherapeutic drug is an alkylating agent, an anti-metabolite, a plant alkaloid, an antibiotic, or a biologic.

15. The method of claim 14, wherein the biologic is a therapeutic antibody.

16. The method of claim 1, wherein said plurality of polypeptides are endogenous to said cell.

* * * * *

SEQUENCE LISTING

<160> NUMBER OF SEQ ID NOS: 21

<210> SEQ ID NO 1
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 1

Glu Asn Leu Tyr Phe Gln Ser Tyr
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2

Ala Ala Gln Thr Ser Pro Ser Pro Lys
1               5

<210> SEQ ID NO 3
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 3

Gly Ser Ala Val Asn Gly Thr Ser Ser Ala Glu Thr Asn Leu Glu Ala
1               5                   10                  15

Leu Gln Lys

<210> SEQ ID NO 4
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 4

Pro Ala Pro Asp Gly Ser Ala Val
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 5

Glu Asn Leu Tyr Phe Gln Ser Lys
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 6

```
Glu Asn Leu Tyr Phe Gln Ser Ala
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 7

Ala Ala Pro Tyr
1

<210> SEQ ID NO 8
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 8

Ala Ala Pro Lys
1

<210> SEQ ID NO 9
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 9

Ala Ala Pro Ala
1

<210> SEQ ID NO 10
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: VARIANT
<222> LOCATION: (2)..(2)
<223> OTHER INFORMATION: Xaa is T or V

<400> SEQUENCE: 10

Glu Xaa Leu Phe Gln Gly Pro
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 11

Asp Asp Asp Asp Lys
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic polypeptide
```

```
<400> SEQUENCE: 12

Leu Val Pro Arg Arg
1               5

<210> SEQ ID NO 13
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 13

Ile Glu Pro Asp
1

<210> SEQ ID NO 14
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 14

Glu Asn Leu Thr Phe Gln Ser
1               5

<210> SEQ ID NO 15
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 15

Gly Ser Ala Val Asn Gly Thr Ser Ser Ala Glu Thr Asn Leu Glu Ala
1               5                   10                  15

Leu Gln Lys

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 16

Pro Ala Pro Asp Gly Ser Ala Val
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 17

Lys Pro Thr Pro Ile Gln Leu Asn
1               5

<210> SEQ ID NO 18
<211> LENGTH: 5
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: VARIANT
<222> LOCATION: (5)..(5)
<223> OTHER INFORMATION: Xaa is G, S or A

<400> SEQUENCE: 18

Asp Glu Val Asp Xaa
1               5

<210> SEQ ID NO 19
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(2)
<223> OTHER INFORMATION: Xaa is Acp
<220> FEATURE:
<221> NAME/KEY: MOD_RES
<222> LOCATION: (13)..(13)
<223> OTHER INFORMATION: C-terminal Tyr modified by esterification with
      glycolate which in turn is esterified with tyrosinamide.

<400> SEQUENCE: 19

Xaa Xaa Gly Gly Thr Glu Asn Leu Tyr Phe Gln Ser Tyr
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 20

Ser Tyr Ala Ala Gln Thr Ser Pro Ser Pro Lys
1               5                   10

<210> SEQ ID NO 21
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 21

Ser Tyr Gly Ser Ala Val Asn Gly Thr Ser Ser Ala Glu Thr Asn Leu
1               5                   10                  15

Glu Ala Leu Gln Lys
            20
```